(12) United States Patent
Van Kampen et al.

(10) Patent No.: US 10,426,624 B2
(45) Date of Patent: Oct. 1, 2019

(54) GLENOSPHERE GUIDE TOOL

(71) Applicant: Zimmer, Inc., Warsaw, IN (US)

(72) Inventors: William Van Kampen, Warsaw, IN (US); Steve Dunstan, Warsaw, IN (US); Jean-Sebastien Merette, Mont-St-Hiliare (CA); Anselm Jakob Neurohr, Montreal (CA)

(73) Assignee: Zimmer, Inc., Warsaw, IN (US)

( * ) Notice: Subject to any disclaimer, the term of this patent is extended or adjusted under 35 U.S.C. 154(b) by 72 days.

(21) Appl. No.: 15/155,840

(22) Filed: May 16, 2016

(65) Prior Publication Data
US 2016/0354209 A1    Dec. 8, 2016

Related U.S. Application Data

(60) Provisional application No. 62/169,839, filed on Jun. 2, 2015.

(51) Int. Cl.
| | | |
|---|---|---|
| *A61F 2/40* | (2006.01) | |
| *A61F 2/46* | (2006.01) | |
| *A61B 17/17* | (2006.01) | |
| *A61F 2/30* | (2006.01) | |

(52) U.S. Cl.
CPC ............ *A61F 2/4081* (2013.01); *A61B 17/17* (2013.01); *A61F 2/40* (2013.01); *A61F 2/4612* (2013.01); *A61F 2/4637* (2013.01); *A61F 2/4684* (2013.01); *A61F 2002/30247* (2013.01); *A61F 2002/30332* (2013.01); *A61F 2002/4085* (2013.01); *A61F 2002/4677* (2013.01); *A61F 2002/4681* (2013.01); *A61F 2002/4687* (2013.01)

(58) Field of Classification Search
CPC .... A61F 2/4081; A61F 2/4612; A61F 2/4637; A61F 2002/30247; A61F 2002/4687; A61B 17/17; A61B 17/1778; A61B 17/1684
See application file for complete search history.

(56) References Cited

U.S. PATENT DOCUMENTS

| | | |
|---|---|---|
| 5,133,765 A | 7/1992 | Cuilleron |
| 5,437,677 A | 8/1995 | Shearer et al. |
| 6,585,771 B1 | 7/2003 | Buttermilch et al. |
| 7,854,768 B2 | 12/2010 | Wiley et al. |
| 7,879,042 B2 | 2/2011 | Long et al. |
| 7,959,680 B2 | 6/2011 | Stone et al. |

(Continued)

*Primary Examiner* — Dinah Baria
(74) *Attorney, Agent, or Firm* — Schwegman Lundberg & Woessner, P.A.

(57) ABSTRACT

Methods and systems include a patient specific instrument for installing a glenosphere within a joint. For example, a method for implanting a glenosphere includes installing first and second pins in a glenoid cavity using a patient specific instrument that sets a distance between the guide pins, installing an implant at the location of the second guide pin, and guiding a glenosphere onto the implant using a helper connected to the first pin. In another example, a glenosphere helper includes a cup shaped body having an interior surface for engaging at least a portion of an outer surface of the glenosphere, and a flange extending from the cup to receive a guide pin at a point, the flange extending from the cup shaped body such that the point is positioned outside a periphery of the glenosphere.

19 Claims, 15 Drawing Sheets

(56) References Cited

U.S. PATENT DOCUMENTS

| | | |
|---|---|---|
| 8,262,677 B2 | 9/2012 | Goto |
| 8,702,717 B2 | 4/2014 | Rauscher et al. |
| 8,900,245 B2 | 12/2014 | Splieth et al. |
| 8,940,054 B2 | 1/2015 | Wiley et al. |
| 9,693,878 B2 * | 7/2017 | Kunz ................. A61B 17/1746 |
| 2006/0058886 A1 * | 3/2006 | Wozencroft ....... A61B 17/1746 623/22.15 |
| 2008/0215156 A1 * | 9/2008 | Duggal .............. A61B 17/1604 623/18.11 |
| 2009/0254093 A1 * | 10/2009 | White ................. A61B 17/175 606/89 |
| 2011/0015639 A1 * | 1/2011 | Metzger .............. A61B 17/175 606/91 |
| 2012/0059383 A1 | 3/2012 | Murphy et al. |
| 2012/0130382 A1 * | 5/2012 | Iannotti ................. A61B 17/15 606/87 |
| 2012/0245647 A1 | 9/2012 | Kunz et al. |
| 2013/0066321 A1 | 3/2013 | Mannss et al. |
| 2013/0110116 A1 | 5/2013 | Kehres et al. |
| 2013/0282129 A1 | 10/2013 | Phipps |
| 2014/0088722 A1 | 3/2014 | Phipps |
| 2015/0073419 A1 | 3/2015 | Couture |
| 2015/0073424 A1 | 3/2015 | Couture |
| 2016/0278932 A1 * | 9/2016 | Merette ................. A61F 2/4081 |

\* cited by examiner

GLENOSPHERE GUIDE TOOL

CLAIM OF PRIORITY

This application claims the benefit of U.S. Provisional Patent Application Ser. No. 62/169,839, filed on Jun. 2, 2015, the benefit of priority of which is claimed hereby, and which is incorporated by reference herein in its entirety.

FIELD

The present subject matter relates to an orthopedic system and specifically to shoulder and reverse shoulder implant systems.

BACKGROUND

In a healthy shoulder, the proximal humerus is generally ball-shaped, and articulates within a socket formed by the scapula, called the glenoid, to form the shoulder joint. Some implant systems for the total replacement of the shoulder joint generally replicate the natural anatomy of the shoulder. Such implant systems can include a humeral component having a stem that fits within the humeral canal, and an articulating head that articulates within the socket of a glenoid component implanted within the glenoid of the scapula.

Reverse-type shoulder implant systems have been developed in which the conventional ball-and-socket configuration that replicates the natural anatomy of the shoulder is reversed, such that a concave recessed articulating component is provided at the proximal end of the humeral component that articulates against a convex portion of a glenosphere of a glenoid component. For example, U.S. Pat. Nos. 7,854,768 and 7,959,680 discuss reverse shoulder systems.

In such reverse shoulder surgeries, implant components are installed on the glenoid portion of the scapula (i.e., shoulder blade) to replicate the shoulder joint. When an implant is installed on the scapula, it is commonly installed in the glenoid cavity, also known as the glenoid or glenoid fossa. The glenoid is a cavity that receives the head of the humerus in an anatomical shoulder. When an implant is used with the glenoid, the base of the implant is located within the glenoid, and could be secured thereto by fasteners such as screws, or using cement and/or fixation peg or keel.

One of the challenges when installing an implant in the glenoid relates to the positioning of implant. Due to the presence of ligaments and like soft tissue, the positioning of the implant must be planned to replicate as much as possible the normal bio-mechanical movements of the humerus relative to the scapula. Another challenge relates to the positioning of the fasteners that secure the implant to the scapula. Indeed, the scapula is relatively thin, and is surrounded by soft tissue. In order for the implant to be solidly secured to the scapula, the screws must be deep enough within the bone material. However, unless desired by the surgeon, the screws must not pierce through the bone surface so as not to damage soft tissue, such as nerves ligaments, tendons, etc.

Patient specific instrumentation (hereinafter "PSI") pertains to the creation of instruments that are made specifically for the patient. PSI are typically manufactured from data using imagery to model bone geometry. Therefore, PSI have surfaces that may contact the bone in a predictable way as such contact surfaces are specifically manufactured to match the surface of a bone. It would therefore be desirable to use PSI technology in shoulder surgery.

Overview

A glenosphere helper is described that facilitates mounting of a glenosphere on a baseplate. The glenosphere helper can help ensure alignment of the components such that, in one example, the glenosphere is properly attached to a baseplate member having Morse taper. Proper alignment of the glenosphere on the baseplate ensures that the glenosphere will properly engage with the glenoid liner component, thereby facilitating proper bio-mechanical functioning and longevity of the prosthesis.

To further illustrate the components and methods disclosed herein, a non-limiting list of examples is provided here:

In Example 1, a glenosphere helper comprises: a body having an interior surface for engaging at least a portion of an outer surface of a glenosphere; and a flange extending from the cup to receive a guide pin at a point, the flange extending from the cup shaped body such that the point is positioned outside a periphery of the glenosphere.

Example 2 can include, or can optionally be combined with the subject matter of Example 1, to optionally include a body having a C-shape.

Example 3 can include, or can optionally be combined with the subject matter of Examples 1 and 2, to optionally include a C-shaped body having a pair of circumferential ends that are configured to be approximately one-hundred-eighty degrees apart around a circumference of the glenosphere.

Example 4 can include, or can optionally be combined with the subject matter of Examples 1-3, to optionally include 4 a flange extending from a middle of the C-shape.

Example 5 can include, or can optionally be combined with the subject matter of Examples 1-4, to optionally include a second flange extending from the body.

Example 6 can include, or can optionally be combined with the subject matter of Examples 1-5, to optionally include a flange and a second flange extending from opposite ends of the C-shape.

Example 7 can include, or can optionally be combined with the subject matter of Examples 1-6, to optionally include a body having a half moon shape that defines an end surface extending circumferentially and radially along an edge of the interior surface.

Example 8 can include, or can optionally be combined with the subject matter of Examples 1-7, to optionally include a guide having a threaded bore, the guide positioned such that the threaded bore is configured to be angled toward the glenosphere.

Example 9 can include, or can optionally be combined with the subject matter of Examples 1-8, to optionally include a point comprising a bore extending through the flange.

Example 10 can include, or can optionally be combined with the subject matter of Examples 1-9, to optionally include a sleeve surrounding the bore.

Example 11 can include, or can optionally be combined with the subject matter of Examples 1-10, to optionally include a guide pin having an outer diameter that is smaller than an inner diameter of the bore.

Example 12 can include, or can optionally be combined with the subject matter of Examples 1-11, to optionally include a body including a cut-out. configured to surround a center location of the glenosphere within the outer surface.

Example 13 can include, or can optionally be combined with the subject matter of Examples 1-12, to optionally include a cut-out having the shape of an impactor head.

Example 14 can include, or can optionally be combined with the subject matter of Examples 1-13, to optionally include an impactor.

Example 15 can include, or can optionally be combined with the subject matter of Examples 1-14, to optionally include a body having a D-shape having a semi-circular end wall into which the cut-out extends.

Example 16 can include, or can optionally be combined with the subject matter of Examples 1-15, to optionally include a body including recesses that form a plurality of prongs.

Example 17 can include, or can optionally be combined with the subject matter of Examples 1-16, to optionally include prongs including a lip configured for retaining the glenosphere within the helper.

Example 18 can include, or can optionally be combined with the subject matter of Examples 1-17, to optionally include a body including a release mechanism configured to move the prongs away from the glenosphere to release the glenosphere from the lips.

Example 19 can include, or can optionally be combined with the subject matter of Examples 1-18, to optionally include a body comprising a polymeric material.

In Example 20, a system for implanting a glenosphere comprises: a glenosphere having an outer surface and a center location; a glenosphere helper having a body comprising: a sidewall for engaging the outer surface around the center location; and a flange extending away from the body beyond a periphery of the glenosphere; and a guide pin extending through the flange.

Example 21 can include, or can optionally be combined with the subject matter of Example 20, to optionally include an impactor configured to engage the center portion of the glenosphere within the sidewall.

Example 22 can include, or can optionally be combined with the subject matter of Examples 20 and 21, to optionally include a sidewall having a cut-out matching a shape of a head of the impactor.

Example 23 can include, or can optionally be combined with the subject matter of Examples 20-22, to optionally include an impactor configured to engage a guide connected to the sidewall of the glenosphere helper.

Example 24 can include, or can optionally be combined with the subject matter of Examples 20-23, to optionally include a flange including a bore configured to form a force fit with the guide pin.

Example 25 can include, or can optionally be combined with the subject matter of Examples 20-24, to optionally include an implant having a tapered surface configured to mate with an interior cavity on the glenosphere.

In Example 26, a method for implanting a glenosphere comprises: installing a first pin in a glenoid cavity; installing an implant in the glenoid cavity; and guiding a glenosphere onto the implant using a helper connected to the first pin.

Example 27 can include, or can optionally be combined with the subject matter of Example 26, to optionally include rotating the helper on the first pin to position the glenosphere toward a mounting surface on the implant; and seating the glenosphere onto the mounting surface of the implant.

Example 28 can include, or can optionally be combined with the subject matter of Examples 26 and 27, to optionally include engaging an impactor on a center area of the glenosphere to seat the glenosphere on the mounting surface; wherein the helper surrounds at least a portion of a periphery of the glenoid to leave the center area uncovered.

Example 29 can include, or can optionally be combined with the subject matter of Examples 26-28, to optionally include engaging an impactor on a guide attached to a sidewall of the helper to seat the glenosphere on the mounting surface.

Example 30 can include, or can optionally be combined with the subject matter of Examples 26-29, to optionally include engaging a release mechanism on the helper to release the helper from the glenosphere after the glenosphere is seated on the mounting surface.

Example 31 can include, or can optionally be combined with the subject matter of Examples 26-30, to optionally include a helper including a flange for engaging the first pin at a bore; and the helper is a patient specific component configured to hold the glenosphere such that a distance between the center area and the bore is equal to the distance.

Example 32 can include, or can optionally be combined with the subject matter of Examples 26-31, to optionally include installing the first guide pin by: connecting a glenosphere trial to the implant; connecting the helper to the glenosphere trial; and installing the first guide pin at a location determined by the helper.

Example 33 can include, or can optionally be combined with the subject matter of Examples 26-32, to optionally include installing the first guide pin by: installing a second guide pin; and using a patient specific instrument that sets a distance between the first and second guide pins.

In Example 34, the device or method of any one or any combination of Examples 1-33 can optionally be configured such that all elements or options recited are available to use or select from.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Example systems and methods for determining a patient specific soft tissue location within a joint of a patient are described. Based at least in part on the patient specific soft tissue locations, the example systems and methods can also be utilized in preoperative planning, to aid in selection or creation of a surgical jig and/or to aid in selection of a prosthesis based on the patient specific soft tissue locations. Furthermore, the systems and methods may incorporate the use of a glenosphere helper or guide tool that facilitates alignment and installation of a glenosphere and a glenosphere baseplate.

Figure 1:
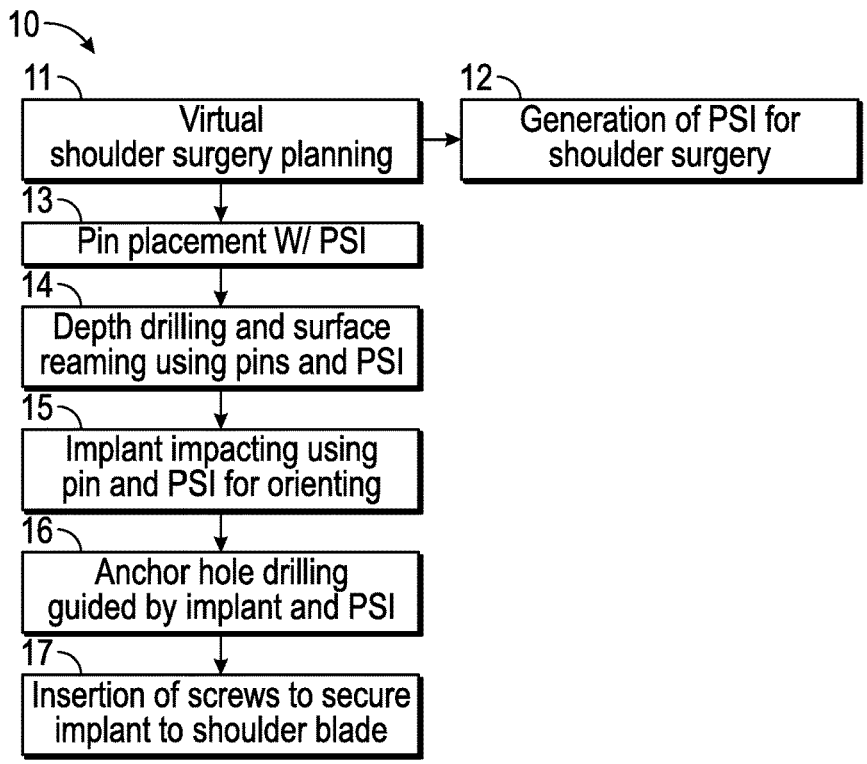
FIG. 1 is a flowchart of a method for securing a glenoid implant on a scapula, using patient specific instrumentation.

Referring to the drawings and more particularly to FIG. 1, there is illustrated at 10 a method for securing a glenoid implant on a scapula (i.e., scapula A). In order to perform the method, patient specific instrumentation of various kinds are used, and will be referred to hereinafter as PSI, with reference to FIGS. 2-22D. By way of example, FIG. 2 features the positioning of a glenoid hemispherical head implant base on the scapula, in reverse total shoulder surgery. However, the method 10 may alternatively be used to secure a cup implant in the glenoid as performed on anatomic total shoulder replacement.

According to step 11 of FIG. 1, virtual shoulder surgery planning is performed. In this planning step, various shoulder structures are displayed as three-dimensional models, along with a model implant and its components. These 3-D models are typically the result of the processing pre-operative imagery (e.g., CT scans, MRI, etc.) and hence are a precise and accurate representation of a patient's bones.

During the planning step, the operator may select various types and dimensions of implants and interactively plan where the implant and its components will be located on the scapula and humerus. In the case of the glenoid implant, the position and orientation thereof may include a virtual representation of the position and orientation of the screws that will secure the glenoid implant to the scapula. Due to the length of the screws and the thinness of the scapula medial to the glenoid, the virtual planning of the location of the glenoid implant typically aims at finding an orientation and depth for the screws that will not have them pierce through the bone material.

Figure 2:
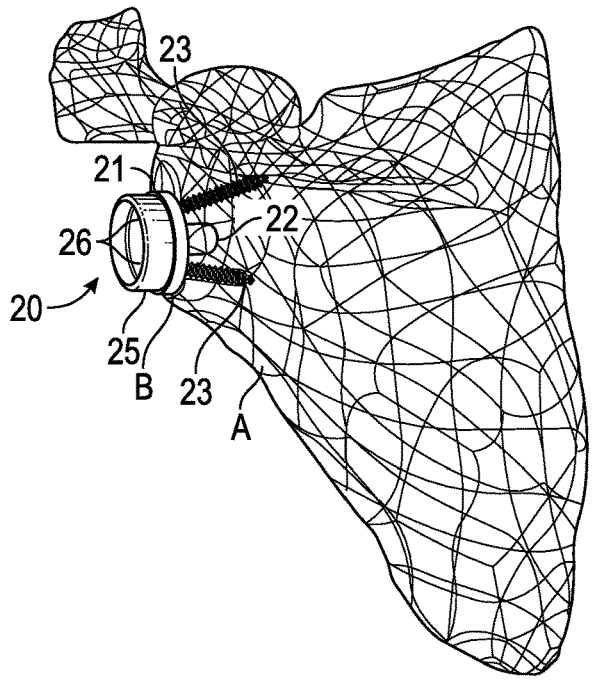
FIG. 2 is a perspective view of a scapula with a glenoid implant, in virtual planning.
Figure 9:
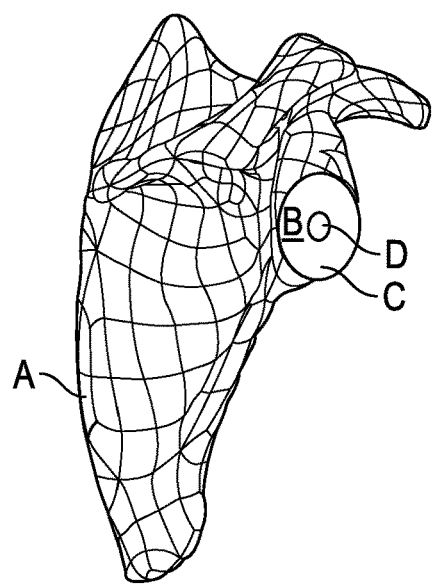
FIG. 9 is a perspective view of the scapula with the reamed glenoid.

For example, there is illustrated at FIG. 2 a model of the scapula A of the patient with parts of an implant 20 (also shown in FIG. 14), the implant 20 being of the ball head or hemispherical head type (i.e., glenosphere 20A). The implant 20 comprises a base plate 21. The base plate 21 is of the type made of a metal that will be adhered and fitted in a resurfaced glenoid cavity C (FIG. 9). For instance, a trabecular-like medical grade metal may be used for the base plate 21. A peg 22 projects from an underside of the base plate 21 and will be accommodated in a bore drilled in the glenoid cavity B. Screws 23 also project from the underside of the base plate 21 and anchor the implant 20 to the scapula A. A body 25 is secured to the base plate 21, as these parts are generally monolithic. The body 25 is the interface of the implant 20 with a hemispherical ball head that will define the surface contacting the humerus or implant thereon. Throughbores 26 are hence concurrently defined in the body 25 and base plate 21, with the screws 23 passing through these throughbores 26.

Steps 12 to 17 of the method 10 are used to guide the surgeon or operator in performing bone alterations so as to replicate the virtual shoulder surgery planning of step 11. Hence, steps 12 to 17 the method 10 are performed to ensure that the glenoid implant is installed substantially similarly to the virtual planning.

Figure 15:
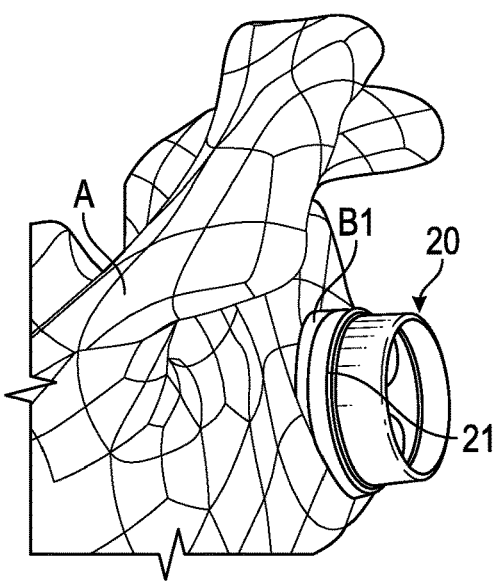
FIG. 15 is a perspective view of the scapula with a glenoid implant and a graft.

According to step 12, PSI are generated using the data obtained from the virtual planning. The PSI will be described in further detail hereinafter. Any appropriate manufacturing method and materials may be used for the PSI, provided that the PSI are precise and accurate representations of the PSI required as a result of the virtual planning. The generation of PSI according to step 12 is performed preoperatively using the imagery data that is also used for the step 11 of virtual shoulder surgery planning. Any other source of anatomical data may also be used, such as manual bone measurements, obtained preoperatively. Another information that may be obtained via the planning step is the generation of a required graft. It may be required to use a graft wedge B1 between the implant and the scapula, and the planning step may therefore define a model of required graft, as shown in FIG. 15, as well as a PSI tool to shape the graft wedge B1 to a predetermined geometry calculated in the virtual planning. The graft wedge B1 would be positioned between the implant 20 and the machined glenoid cavity C. The use of a graft may be required for scapulas limited to a shallow glenoid cavity C, i.e., that does not have a full counterbore shape. Hence, as shown in FIG. 15, the graft wedge B1 would form concurrently with the cavity C the surface against which the implant 20 is applied.

Steps 13 to 17 are performed intra-operatively. The steps are performed once the shoulder joint has been exposed and the humerus has been dislocated, resected and/or separated from the scapula A (FIG. 2).

Figure 3:
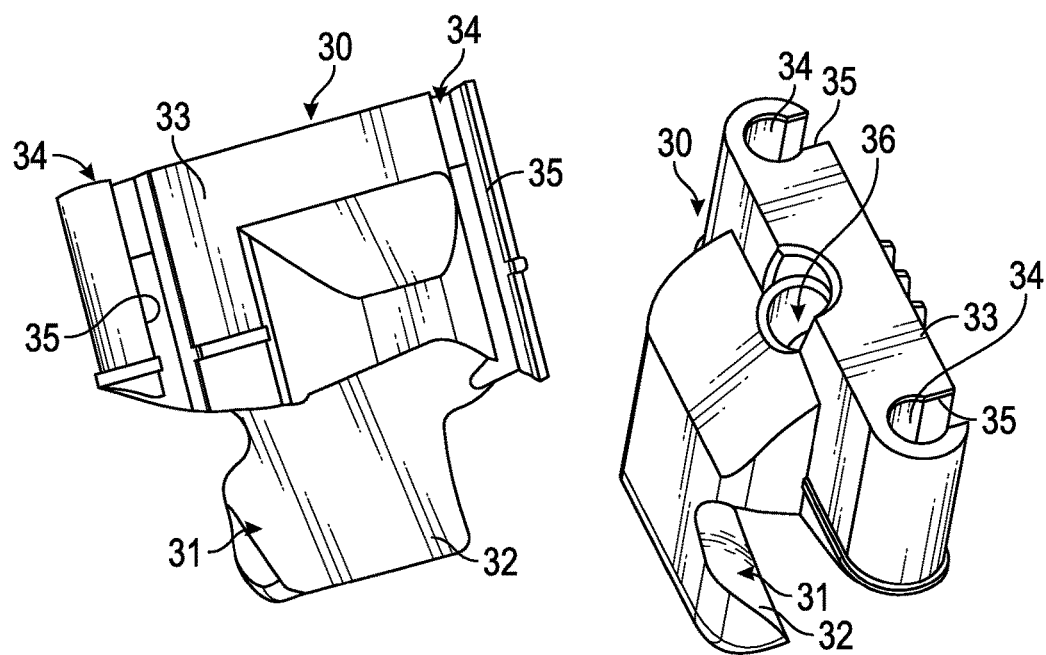
FIG. 3 is a pair of perspective views of a pin placement PSI in accordance with an embodiment of the present disclosure.
Figure 4:
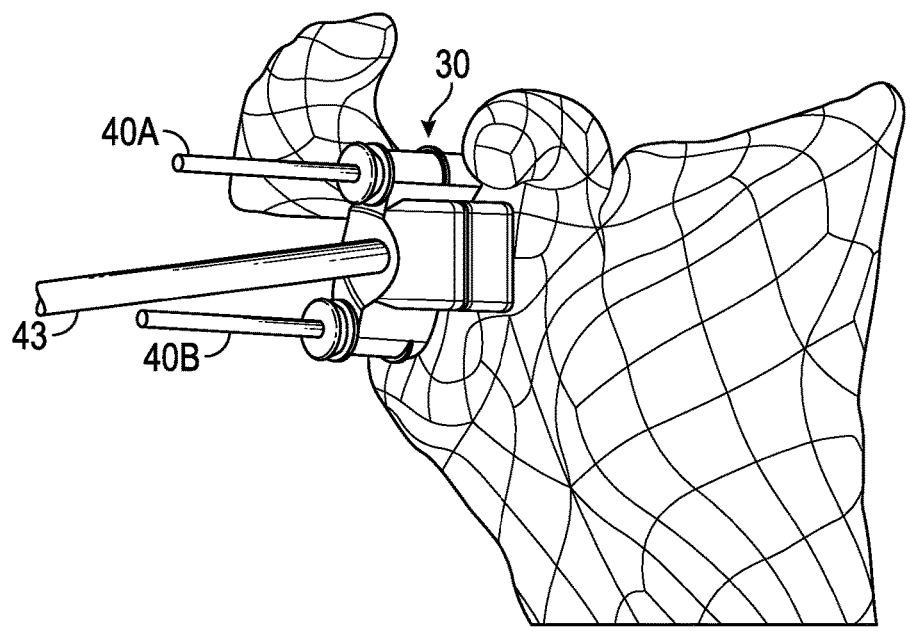
FIG. 4 is a perspective view of the scapula with the pin placement PSI of FIG. 3, during placement of pins.
Figure 5A:
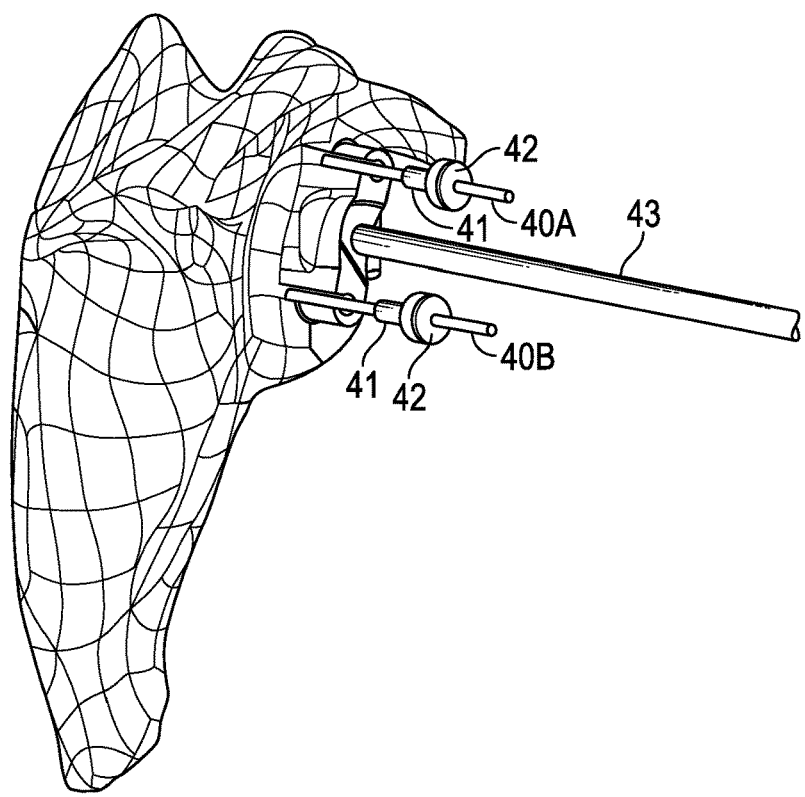
FIG. 5A is a perspective view of the scapula of FIG. 4, during the removal of the pin placement PSI.
Figure 5B:
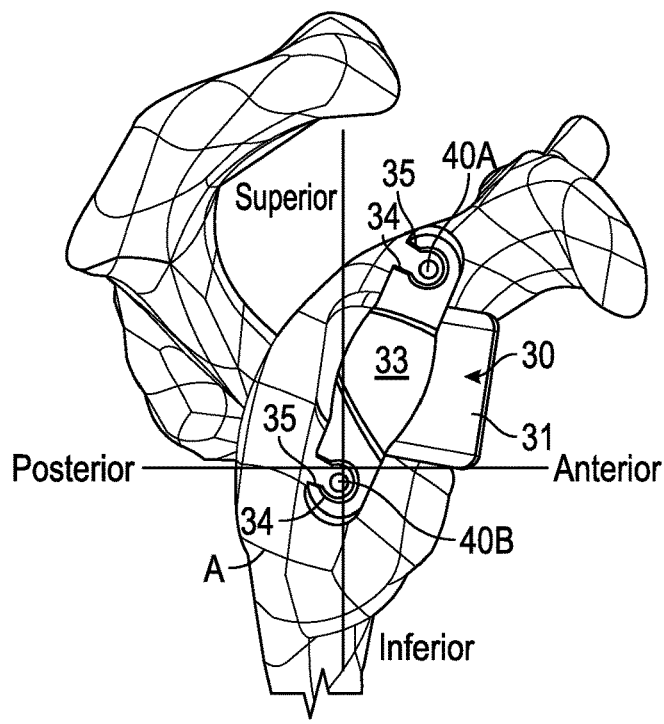
FIG. 5B is a lateral view of a pin placement PSI of FIG. 4, on the scapula.

According to step 13 (FIG. 1), a pair of pins are placed in the scapula A using PSI. Referring concurrently to FIGS. 3 and 4, a pin placement PSI is generally shown at 30. The pin placement PSI 30 comprises an anatomical interface 31. The anatomical interface 31 has a laterally opened hook-like shape so as to receive therein both sides of the scapula head and/or neck of the glenoid B. In accordance with PSI, the anatomical interface 31 has a contact surface(s) 32 that is manufactured to match the corresponding surface on the patient's scapula. Accordingly, the positioning of the pin placement PSI 30 will be guided by the contact surface 32 finding its corresponding matching surface on the scapula A.

The pin placement PSI 30 further comprises a drill guide 33. The drill guide 33 is positioned relative to the anatomical interface 31 as a function of the virtual planning of step 11 (FIG. 1). The drill guide 33 has a pair of cylindrical cutouts or slots 34 that are specifically positioned and oriented to guide the drilling of the pins in the glenoid B, i.e., the slots 34 extend in the longitudinal direction of the PSI 30. According to an embodiment, lateral openings 35 allow lateral access to the slots 34 such that the pins may be laterally inserted into the slots 34. A socket 36 or like connector may also defined in the drill guide 33 to facilitate the manipulation of the pin placement PSI 30. For instance, an elongated tool may be connected to the pin placement PSI 30 by way of the socket 36, for its distal manipulation.

As shown concurrently in FIGS. 4 and 5, superior pin 40A and inferior pin 40B are drilled into the scapula A. The pins 40A and 40B may be provided with sleeves 41 (a.k.a., bushings) received in a planned fit (e.g., precise fit) that will ensure that the pins 40A and 40B are axially centered in the slots 34, as the sleeves 41 have throughbores centered with the slots 34. Moreover, the sleeves 41 may comprise abutment ends 42 to control the depth of insertion of the pins 40A and 40B in the glenoid. Any appropriate methods are also considered to control the depth of insertion of the pins 40A and 40B, such as graduating the pins 40A and 40B with a scale, etc.

In operation, handle 43 is connected to the socket (FIGS. 3 and 4), and the pin placement PSI 30 is installed onto the glenoid B with the anatomical interface ensuring that the pin placement PSI 30 is properly positioned on the scapula A, by laterally moving the pin placement PSI 30 into planned position on the bone. The pins 40A and 40B with sleeves 41 thereon are inserted in the slots 34 of the pin placement PSI 30 via the lateral openings 35, and may hence be drilled into the glenoid B, or the sleeves/bushings 41 may be placed in the slots 34 prior to threading the pins 40A and 40B therein. Once the pins 40A and 40B are suitably inserted in the scapula A, the sleeves 41 may be withdrawn by sliding them off the end of the pins 40A and 40B shown in FIG. 5A, thereby allowing the removal of the pin placement PSI 30 from the scapula A by a lateral movement. The surfaces of the hook-like portion of the anatomical interface 31 are generally transverse to a longitudinal direction of the drill guide 33. The presence of the lateral openings 35 allows a good contact surface between the hook-like portion of the anatomical interface 31, without having difficulties in the lateral withdrawal of the PSI 30 as the pins 40A and 40B pass through the lateral openings 35.

According to the illustrated embodiment, one of the pins, superior pin 40B, is at a center of the anticipated resurfaced glenoid cavity C, while the other pin, inferior pin 40A, is located adjacent to the superior glenoid rim in alignment with the coracoid or at the base of the coracoid. Other positions are also considered. For illustrative purposes, a contemplated position of the pin placement PSI 30 is generally shown relative to the scapula A in FIG. 5B.

Figure 6:
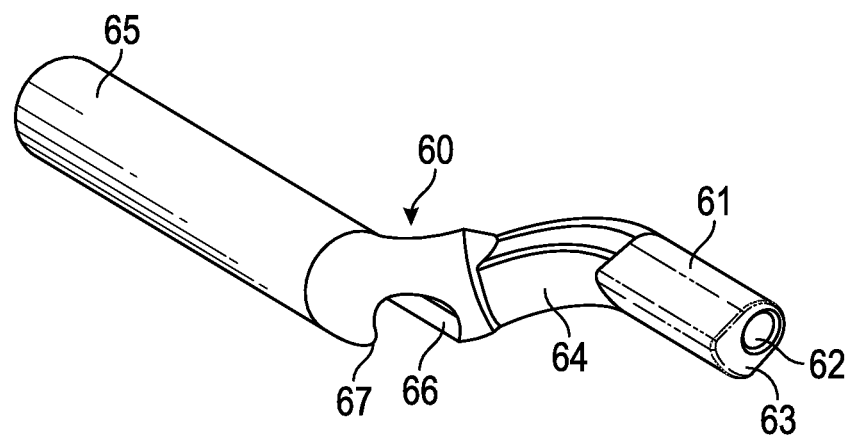
FIG. 6 is a perspective view of a depth drilling PSI in accordance with another embodiment of the present disclosure.
Figure 7:
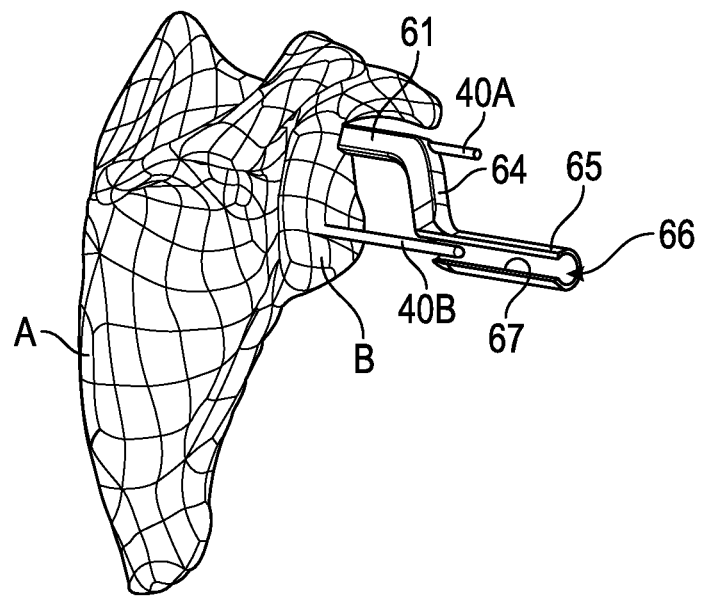
FIG. 7 is a perspective view of the scapula with the depth drilling PSI of FIG. 6.

Referring to FIG. 1, a step 14 of depth drilling and/or surface reaming on the glenoid B is performed using the pins 40A and 40B and an appropriate PSI. Referring concurrently to FIGS. 6 and 7, a reaming PSI is generally shown at 60. The reaming PSI 60 has a first tube 61 with a pin slot 62 that is dimensioned to be slid onto superior pin 40A, thereby forming a cylindrical joint therewith. An end of the first tube 61 defines an abutment 63 to abut against the scapula A. A spacing arm 64 extends laterally from the first tube 61 and has at its free end a second tube 65. The second tube 65 also comprises a shaft slot 66, which shaft slot 66 is laterally accessible via a lateral opening 67, used to rotate the reaming PSI 60 such that the inferior pin 40B enters the shaft slot 66. As the reaming PSI 60 is patient specific, the pin slots 62 and the shaft slot 66 are spaced apart by a predetermined distance to match the spacing between the pins 40A and 40B. Hence, as shown in FIG. 7, when the first tube 61 is slid onto superior pin 40A, inferior pin 40B may be oriented to be within the shaft slot 66 of the second tube 65.

It is pointed out that step 14 may comprise a verification of the location of the pins 40A and 40B. As the reaming PSI 60 is fabricated to receive the pins 40A and 40B, the centrally-located pin 40B should be axially centered in the second tube 65. Any off-centering may indicate improper positioning of the pin 40B, and such indication may cause a review of step 13 to reposition the pins 40A and 40B.

Figure 8:
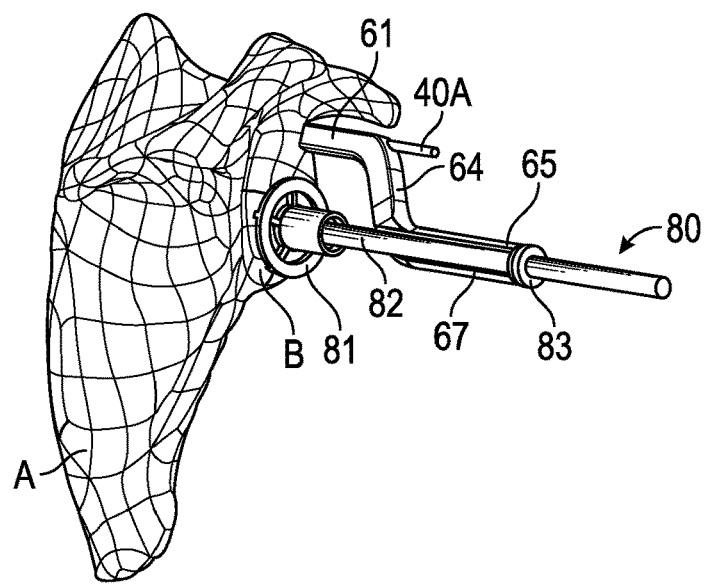
FIG. 8 is a perspective view of the scapula and depth drilling PSI, with a cannulated reamer.

Referring to FIG. 8, a cannulated reamer 80 may therefore be installed onto the pin 40B that is within the shaft slot 66, so as to be coaxially guided by the pin 40B in translation. The reamer 80 has a reamer end 81 that is selected to perform resurfacing of a planned diameter in the glenoid B. The reamer end 81 is located at the end of a shaft 82. The shaft 82 is sized to be received in the shaft slot 66 of the reaming PSI 60, to form the translational joint. Moreover, the reamer end 81 may also drill a bore of sufficient diameter to receive the peg 22 of the implant 20 therein (FIG. 2), to a depth defined by abutment against the reaming PSI 60. The drilling of the peg bore may alternatively be done separately. Accordingly, the combination of the pin 40B in the cannulated reamer 80 and the cooperation between the shaft 82 and the shaft slot 66 ensures that the glenoid B is reamed specifically where desired to a desired depth. The shaft 82 enters the shaft slot 66 by being slid or snapped into it. Still referring to FIG. 8, a stopper 83 may be installed on the end of the shaft 82. The stopper 83 cooperates with the reaming PSI 60 to limit the depth of penetration of the reamer 80 in the glenoid B, to ensure that the surface reaming and optional depth drilling (if done separately for the peg 22 of FIG. 2) have a planned depth.

It is observed that both pins 40A and 40B are used to support the reaming PSI 60 and guide movement of the cannulated reamer 80. By using both pins 40A and 40B, the structural integrity of the assembly of pin 40A, pin 40B and PSI 60 is increased over a single pin. However, it is considered to use any other configuration, for instance using a single pin 40B, with the cannulated reamer 80, in order to ream the glenoid B. For example, U.S. Pat. No. 8,523,867 to Rauscher et al., which is hereby incorporated by reference in its entirety for all purposes, describes a reaming process that utilizes a single guide pin inserted into the glenoid cavity. In such cases, a single pin 40A, for example, can be inserted at a later time to carry out subsequent procedures, such as is described with reference to FIGS. 17 and 18.

As shown in FIG. 9, once the glenoid B has been reamed to define the resurfaced glenoid cavity C with peg bore D, the depth drilling PSI 60 may be removed along with the pins 40A and 40B. Although not shown, it may be desired to keep the pin 40A that is not in the resurfaced glenoid cavity C, as explained hereinafter. In the case in which the wedge graft B1 is used (FIG. 15), the wedge graft B1 is installed at the adequate position on the glenoid B, adjacent to the resurfaced glenoid cavity C. The pin 40A on the coracoid may be used to guide an operator in properly orienting the wedge graft B1. The wedge graft B1 may be fused to the glenoid B, and the screws 23 will secure both the implant 20 and the wedge graft B1 to the glenoid B. Additionally, glenosphere 20A may be installed on body 25 of baseplate 21, as discussed with reference to FIGS. 17 and 18, using a helper that slides along superior pin 40A.

Referring to FIG. 1, a step 15 of impacting the implant 20 is performed, using one of the pins and PSI for properly orienting the implant 20. More specifically, the orientation of the implant 20 will have an impact on the positioning of the screws 23 (FIG. 2). Hence, in order to replicate the virtual planning of step 11, the implant 20 must be correctly oriented so as to have the throughbores 26 aligned with the planned location of insertion of the screws 23.

Figure 10:
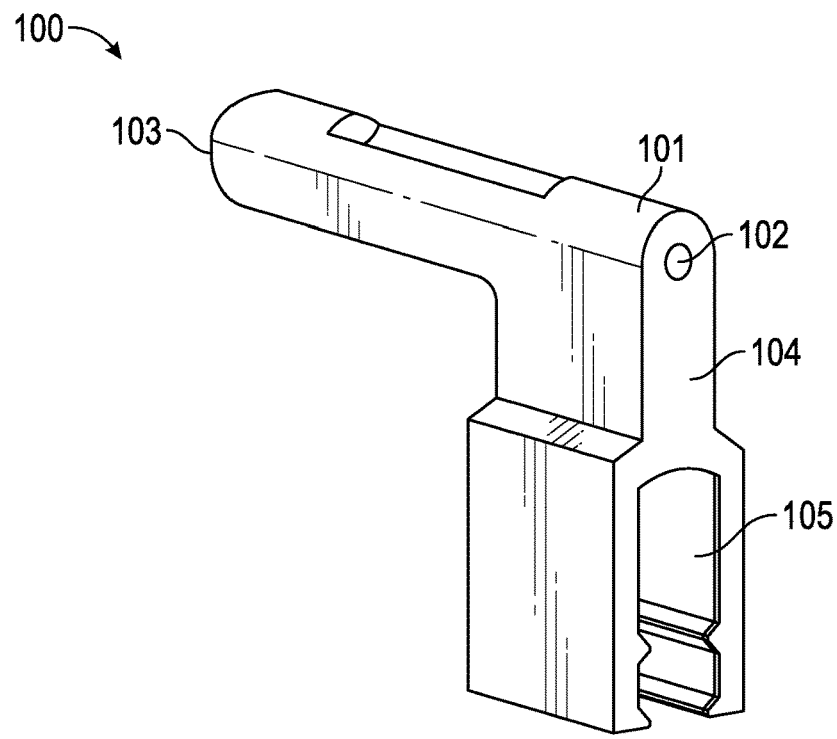
FIG. 10 is a perspective view of an impactor guide PSI in accordance with yet another embodiment of the present disclosure.
Figure 11:
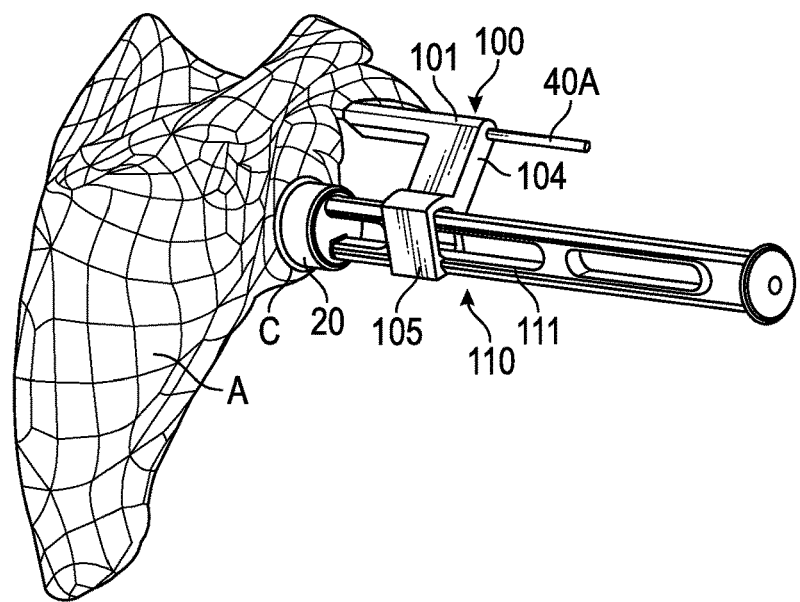
FIG. 11 is a perspective view of the scapula with the impactor guide PSI and impactor tool.

Referring concurrently to FIGS. 10 and 11, an impacting guide PSI is generally shown at 100. The impacting guide PSI 100 comprises a tube 101 with a pin slot 102. The pin slot 102 is sized so as to receive therein the remaining pin 40A and form therewith a cylindrical joint. An abutment end (with any appropriate shape/geometry) 103 of the tube may have a patient-specific contact surface shaped to rest against a surrounding bone surface and hence prevent rotation of the PSI 100 when the tube 101 abuts the bone. An arm 104 projects laterally from the tube 101. A guide bracket 105 is at a free end of the arm 104 and is used to guide the movement of an impactor tool 110. More specifically, the guide bracket 105 has a lateral opening for receiving therein a shaft 111 of the impactor tool 110 to form a sliding joint therewith.

The impactor tool 110 may be conventional, with a pair of pegs spaced apart to be received in the throughbores 26 of the implant 20 (FIG. 2). The guide bracket 105 is specifically oriented as a function of a location of these pegs at the end of the shaft 111 of the impactor tool 110, to control the positioning of the throughbores 26 of the implant 20, in accordance with the virtual planning step 11 (FIG. 1).

Hence, with the assembly of FIG. 11, the implant 20 may be inserted into the resurfaced glenoid cavity C. The matching shape of the implant 20 and resurfaced glenoid cavity C may result in a self-centering of the implant 20 during impacting (and therefore not necessitating the patient-specific surface at the abutment end 103 to perform an alignment). However, the PSI 100 and impactor tool 110 generally ensure that the implant 20 is fully inserted in the resurfaced glenoid cavity C, with the throughbores 26 located where planned. At this point, the PSI 100 may be removed with the impactor tool 110 leaving the implant 20 in the resurfaced glenoid cavity C.

Figure 12:
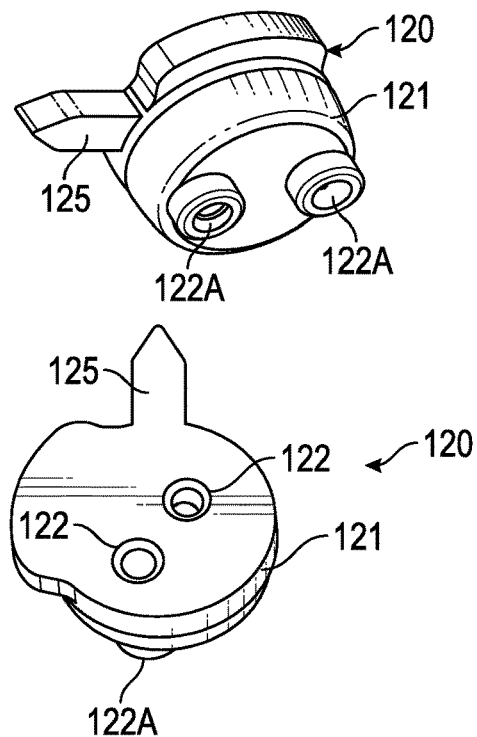
FIG. 12 is a perspective view of a drilling guide PSI in accordance with yet another embodiment of the present disclosure.
Figure 13:
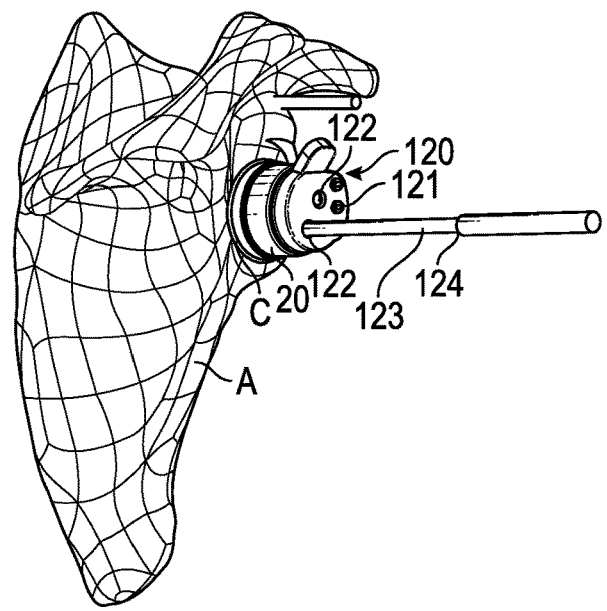
FIG. 13 is a perspective view of the scapula with the drilling guide PSI and drill bit.
Figure 14:
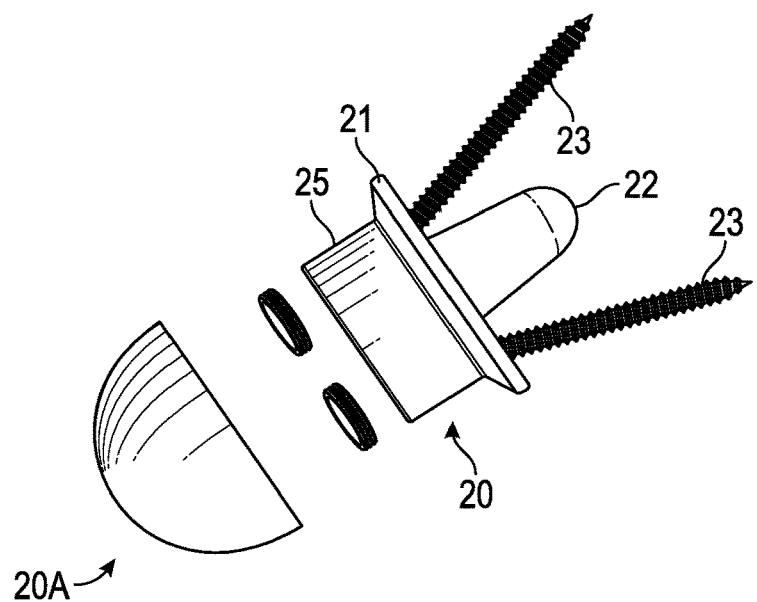
FIG. 14 is an assembly view of a glenoid hemispherical implant.

According to step 16 of FIG. 1, anchor holes may be drilled in the glenoid as planned, for the subsequent insertion of the screws 23. Referring to FIGS. 12 and 13, a drill guide PSI 120 has a body 121 sized to be received in a corresponding cavity in the implant body 25. A pair of drill guide bores 122 are defined in the body 121 of the drill guide PSI 120. The drill guides bores 122 are specifically located and oriented to have guiding cylinders 122A in axial extension of the throughbores 26 in the implant 20 (FIG. 2). Moreover, the diameter of the guiding cylinders 122A is generally tapering to center a drill bit 123 therein, to reduce any potential play between the drill bit 123 and the drill guide bores 122. The material used for the body 121 of the drill guide PSI 120 may also be selected so as not to be damaged by the drill bit 123. As shown in FIG. 13, a stopper 124 may be provided on the drill bit 123 to control the drilling depth to reach the planned depth for the anchor holes. Alternative methods are considered as well, such as graduating the drill bit 123 with a scale, to control the depth. Once the anchor holes have been drilled, the drill guide PSI 120 may be removed. As shown in FIG. 12, the drill guide PSI 120 may also comprise a visual pointer 125. The visual pointer 125 may be patient-specifically formed in the drill guide PSI 120 to point at the remaining pin. This therefore represents an additional verification step to ensure that the holes are drilled at the desired location.

According to step 17 of FIG. 1, screws 23 (or like fasteners) may secure the implant 20 to the scapula A, replicating the virtual planning of FIG. 2. Additional steps can then be performed to finalize the shoulder surgery.

It is pointed out that the method 10 may include a step of creating the graft B1 of FIG. 15. The step of method 10 may include providing a PSI tool for the removal of bone material, for instance from the humerus, as the humerus must be resurfaced. However, the graft B1 removed from the humerus or other bone may simply have a cylindrical shape, and hence a standard cylindrical reamer of appropriate diameter may be used. As the graft B1 is shown as having a wedge shape in FIG. 15, an appropriate PSI tool may be created to machine the oblique plane of the graft B1.

Figure 16A:
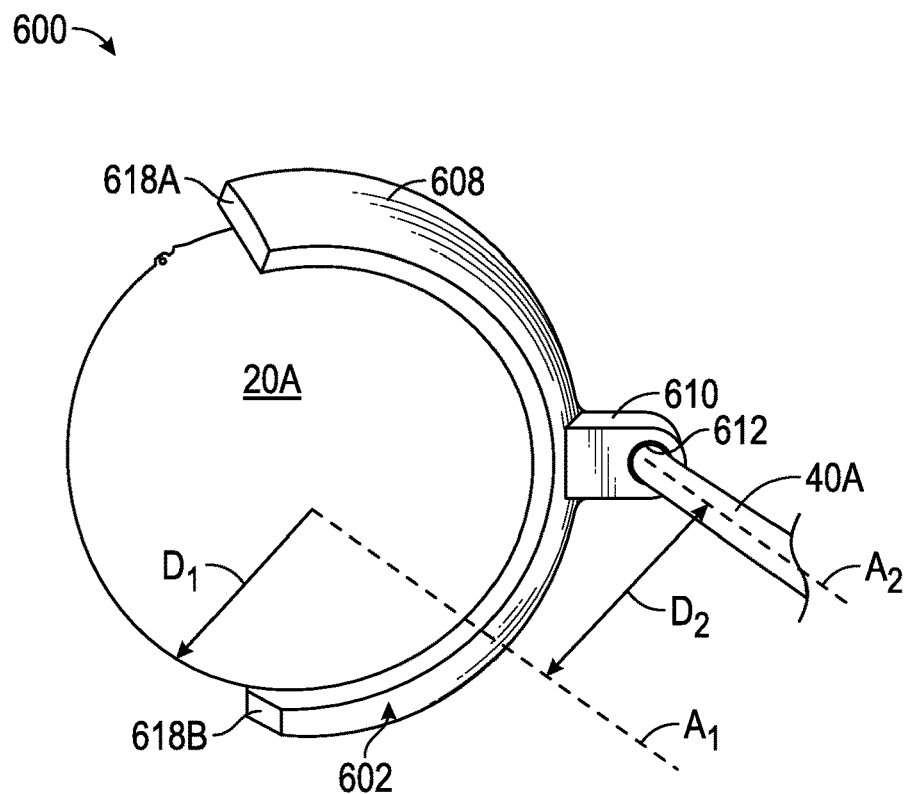
FIG. 16A is a perspective view of a glenosphere helper showing a C-shaped helper body coupled to a glenosphere and a superior pin.

FIG. 16A is a perspective view of glenosphere helper 600 showing C-shaped helper body 602 coupled to glenosphere 20A and superior pin 40A. Helper body 602 can include sidewall 608 and flange 610, which can include bore 612. Sidewall 608 can include interior surface 614, exterior surface 616 and ends 618A and 618B.

Glenosphere 20A can be accurately positioned and installed on implant 20 (FIG. 15) using glenosphere helper 600, which slides along superior pin 40A. In various examples, superior pin 40A can be left in place, such as after the impacting performed with reference to FIG. 11 using impacting guide PSI 100. The known relationship between superior pin 40A and inferior pin 40B, which is removed so implant 20 can be installed, can be incorporated into the design of helper 600 in order to properly seat glenosphere 20A on implant 20.

Superior pin 40A can be fabricated from a medical grade material, such as stainless steel. Glenosphere helper 600 can be fabricated from a biocompatible plastic or polymer, such as polyvinylchloride (PVC) or polyetheretherketone (PEEK), that prevents scratching or damaging of glenosphere 20A. In one example, glenosphere helper 600 can be fabricated from DuraForm® nylon material commercially available from 3D Systems, Inc. In other examples, glenosphere helper 600 can be fabricated from a ceramic, a metal, a polymer, or combinations thereof. Glenosphere helper 600 may also be fabricated using 3D printing techniques, in other examples. For example, glenosphere helper 600 may be a PSI component that is fabricated using rapid manufacturing techniques based off of a 3-D patient model to match pre-planned surgeon specifications.

Figure 16B:
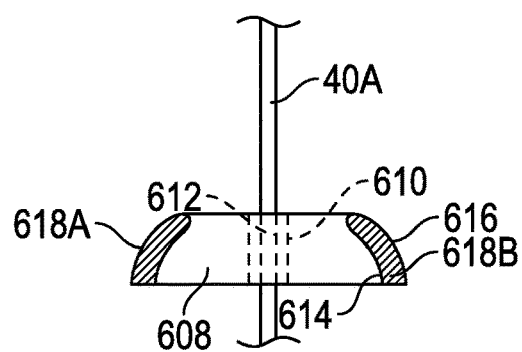
FIG. 16B is a side view of the glenosphere helper of FIG. 16A showing the shape of a sidewall.

In the example of FIGS. 16A and 16B, helper body 602 can be C-shaped so that ends 618A and 618B form circumferential facing surfaces that can be one-hundred-eighty degrees apart. As such, sidewall 608 can wrap around, or surround, center axis $A_1$ of glenosphere 20A. In such an example, end surfaces 618A and 618B can be diametrically opposed with respect to center axis $A_1$. In other examples, sidewall 608 can have a length that positions end surfaces 618A and 618B closer together (e.g. less than one-hundred-eighty degrees) or farther apart (e.g. greater than one-hundred-eighty degrees).

Superior pin 40A can have a round cross-section with a diameter that is commonly used in orthopedic medical procedures. For example, pin 40A can have a diameter of 2.5 mm. In other examples, pin 40A can have other diameters that mate with other sized helper bores, as discussed below. Bore 612 can be sized to have a diameter that closely matches the diameter of pin 40A such that a force fit or interference fit is formed. Flange 610 can slide freely on pin 40A, but is also tightly disposed on pin 40A so that helper 600 and glenosphere 20A can remain in a set position on pin 40A without additional external support. As discussed below with regard to other examples, flange 610 can include a sleeve that additionally lengthens bore 612 to provide further support.

In the example shown, flange 610 is located halfway between ends 618A and 618B on exterior surface 616 of sidewall 608. Flange 610 can extend from the exterior of sidewall 608 so that bore 612 is located outside of the outer perimeter, or diameter $D_1$, of glenosphere 20A, as well as being outside the outer perimeter of sidewall 608. In one example, a center axis of bore 612 is disposed parallel to the center axis $A_1$ of glenosphere 20A so that the center axis of bore 612 does not extend into glenosphere 20A. As will be discussed in greater detail below, flange 610 is located away from the interior region of sidewall 608 to permit an impactor access to glenosphere 20A at axis $A_1$. Flange 610 can be approximately as tall as sidewall 608 (see FIG. 6B) to provide stability to helper body 602 when connected to pin 40A. For example, the height of sidewall 608 prevents rocking of helper body 602 on pin 40A.

Axis $A_2$ of pin 40A can be disposed parallel to center axis $A_1$ of glenosphere 20A so that helper 600 will slide along pin 40A straight towards the baseplate to which it is to be mounted, as discussed with reference to FIGS. 17 and 18. The distance $D_2$ between axis $A_2$ of superior pin 40A and center axis $A_1$ of glenosphere 20A can be determined using three-dimensional (3D) imaging techniques and, thus, in some examples, may comprise a patient specific instrument (PSI), as will be discussed below in greater detail. However, in other examples, glenosphere helper 600 is not a PSI and can be produced without the aid of pre-operative imaging.

FIG. 16B is a side view of glenosphere helper 600 of FIG. 6A showing the shape of sidewall 608. Sidewall 608 can be curved so that helper body 602 has a cup shape. The outer surface of glenosphere 20A (shown in FIG. 6A) has a hemispherical shape that mates with inverse-hemispherical articulating liner 108 (FIG. 1). Inner surface 614 of sidewall 608 can match the outer contour of glenosphere 20A. As such, when glenosphere 20A is positioned inside helper 600, glenosphere 20A will be held in place by friction. Outer surface 616 of sidewall 608 can have any shape and, in the illustrated example, has a hemispherical curvature with a slightly larger diameter than inner surface 614.

Figure 17:
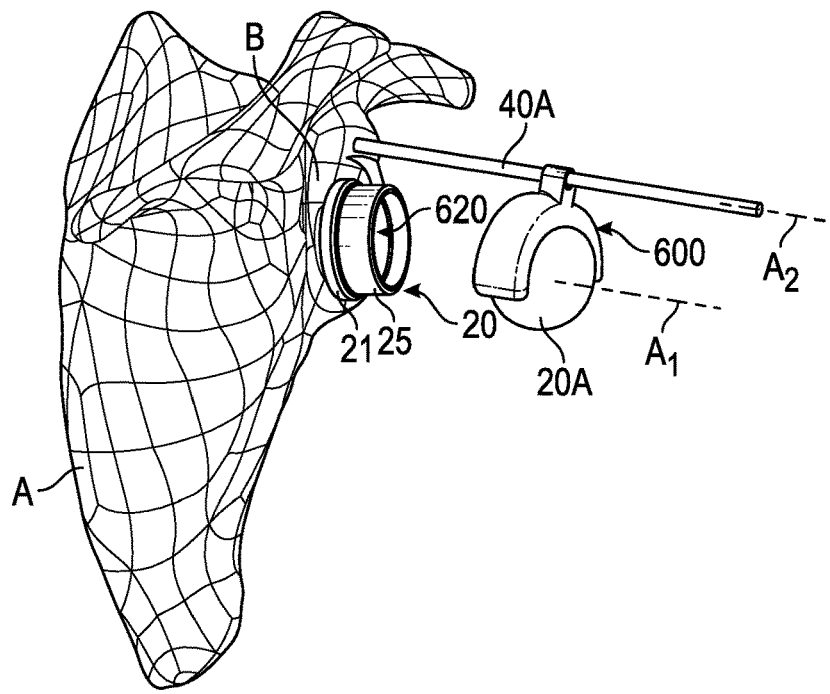
FIG. 17 is a perspective view of the scapula having a glenoid cavity to which is attached a glenosphere baseplate and a superior pin that supports a glenosphere helper.

FIG. 17 is a perspective view of scapula A having glenoid cavity B into which is inserted superior pin 40A. Additionally, implant 20 is installed on glenoid cavity B, which was previously reamed along the axis of inferior pin 40B (FIG. 4), as is discussed with reference to FIG. 8. Glenosphere 20A is held by helper 600 connected to superior pin 40A. As discussed above, pin 40A may be installed as part of a patient specific implant procedure where pins 40A and 40B are installed prior to reaming and installation of the implant 20 using PSI 30. However, in other examples, superior pin 40A may be installed after implant 20 is installed for the dedicated purpose of installing glenosphere 20A. Such procedures may comprise standalone, non-PSI procedures that does not, for example, require pre-operative imaging. For example, glenosphere helper 600 may be used to install superior pin 40A in the correct location. In one example, a glenosphere trial (not shown) can be used to assist in installing superior pin 40A. The trial has a slightly larger diameter than body 25 so that it can be easily connected to and removed from implant 20. Thus, the trial can be placed on implant 20 and helper 600 can be placed on the trial so that bore 612 can be placed to proper distance from glenosphere 20A via flange 610.

In order to perform a shoulder replacement arthroplasty, such as a reverse shoulder implant, glenoid cavity B is prepared to receive glenoid baseplate 21 to which a glenosphere 20A can be mounted. The location of superior pin 40A is known relative to the location of inferior pin 40B so that superior pin 40A may serve as a reference for operations conducted at the location of inferior pin 40B after inferior pin 40B is removed. Glenoid cavity B is bored-out along the axis of inferior pin 40B, as discussed above with reference to FIG. 8, to receive peg 22 (FIG. 14) in peg bore D (FIG. 9), using superior pin 40A as a guide.

The distance between superior pin 40A and inferior pin 40B can be equal to distance $D_2$ (FIG. 16A), which is the distance between center axis $A_1$ of glenosphere 20A and pin 40A. The location for center axis $A_1$ of glenosphere 20A can be determined pre-operatively using three-dimensional (3D) imaging and mapping techniques that generate a model of scapula A to determine the point of articulation for the humerus in glenoid cavity B, as is discussed above. Thus, the location of inferior pin 40B can be selected to coincide with the point of articulation on axis $A_1$. Additionally, the location of pins 40A and 40B can be selected so that the pins will be supported by sufficient bone mass of scapula A.

Implant 20 can include baseplate 21 and body 25, which includes passage 620. Baseplate 21 can be attached to glenoid cavity B via threaded fasteners 23 inserted into passage 620 and through bores in baseplate 21, such as is shown in FIG. 2. Body 25 extends from baseplate 21 and is configured to be received by a mating cavity (see, e.g., FIG. 20B) on the back side of glenosphere 20A. In one example, body 25 is configured to have a Morse taper and glenosphere 20A is configured to have a mating recess such that a self-holding connection is made. Such a configuration is discussed in greater detail in U.S. Pub. No. 2013/0282129 to Phipps, which is hereby incorporated by reference in its entirety for all purposes. In other examples, baseplates having other locking mechanisms can be used, such as described in U.S. Pat. No. 8,940,054 to Wiley et al., which is hereby incorporated by reference in its entirety for all purposes. In another example, a simple ribbed connection can be used wherein the post includes shallow ribs that interlock with opposite shallow ribs on the interior of the glenosphere.

With any manner of connecting glenosphere 20A to baseplate 21, it can be desirable that the components be properly aligned such that the prosthetic shoulder functions as precisely as possible. Additionally, it can be desirable for glenosphere 20A to remain unblemished, e.g. unscratched, during the implantation process in order to increase the smoothness and longevity of the prosthetic joint. Furthermore, if the glenosphere 20A were somehow pushed onto body 25 off-axis, it may be possible to damage body 25 or it may be impossible to remove glenosphere 20A from body 254 for reseating without damaging body 25. As such, it can be desirable to ensure that glenosphere 20A is installed, e.g. pushed, onto body 25 in the proper orientation. Helper 600 accomplishes this by automatically aligning the centers of glenosphere 20A and body 25. As such, axis $A_1$ of the center of glenosphere 20A is arranged parallel to axis $A_2$ of superior pin 40A to facilitate sliding of helper 600 along pin 40A to guide glenosphere 20A onto baseplate 21.

Figure 18:
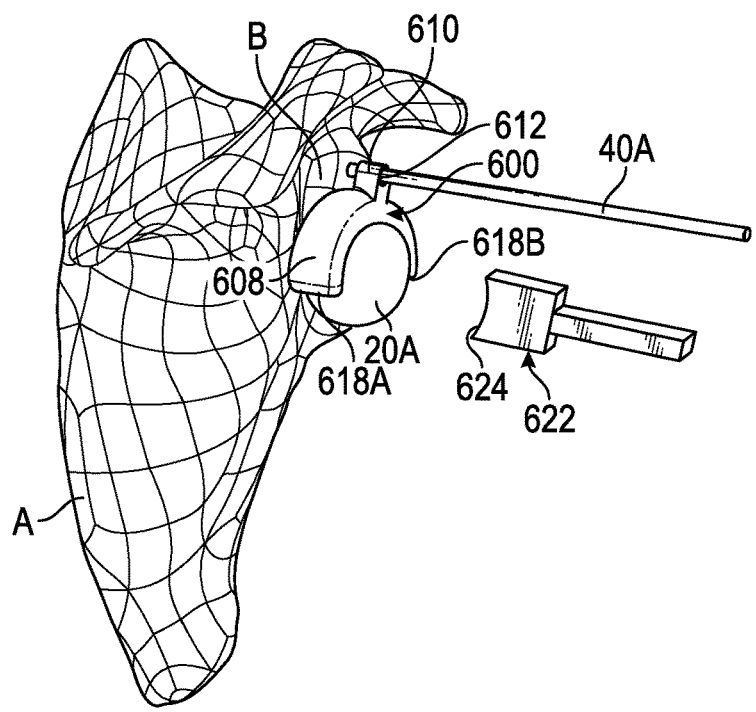
FIG. 18 is perspective view of the scapula of FIG. 17 showing the glenosphere helper advanced on the superior pin to engage the glenosphere with the baseplate and ready to receive an impactor.

FIG. 18 is perspective view of scapula A of FIG. 17 in which baseplate 21 is installed in place of inferior pin 40B and glenosphere 20A is held by helper 600 connected to superior pin 40A. Impactor 622 can be positioned to engage glenosphere 20A between ends 618A and 618B.

From the position of FIG. 17, helper 600 is slid down pin 40A towards baseplate 21, in the direction of scapula A. Initially, helper 600 can be oriented on pin 40A so that ends 618A and 618B are facing the anterior direction (toward the left in FIG. 18). When glenosphere 20A is positioned close to the patient, so as to be entering the incision for the procedure, helper 600 can be rotated clockwise down toward baseplate 21. As such, flange 610 can be long enough to bridge the gap between helper body 602 and superior pin 40A with glenosphere 20A disposed along axis $A_1$, while also locating bore 612 outside of the perimeter of sidewall 608. Helper 600 can continue to be advanced toward scapula A until it is positioned over body 25. At such point, glenosphere 20A can be felt to "suck down" on glenosphere 20A, particularly in examples using a Morse taper. In addition to aiding proper Morse taper engagement, glenosphere helper 600 helps ensure proper angle of impact. For example, helper 600 facilitates straight line engagement of the glenosphere socket onto body 25, which helps eliminate damage to those surfaces that has the potential to weaken the connection therebetween.

With glenosphere 20A positioned on body 25 using helper 600, impactor 622 can be brought into engagement with the outer surface of glenosphere 20A so that glenosphere 20A can be driven down on body 25 into full engagement with baseplate 21. Impactor 622 can have curved surface 624 that can be configured to engage flush with glenosphere 20A. Surface 624 can fit within the interior of helper body 602 defined by sidewall 608. As such, helper 600 does not interfere with impaction, particularly along axis $A_1$ of the center of glenosphere 20A. Helper 600 can remain in place and can hold glenosphere 20A in the proper position over baseplate 21 so that proper seating between body 25 and glenosphere can be obtained by impaction. Subsequent to impaction, helper 600 can be removed from pin 40A, and pin 40A can be removed from glenoid cavity B.

Figure 19A:
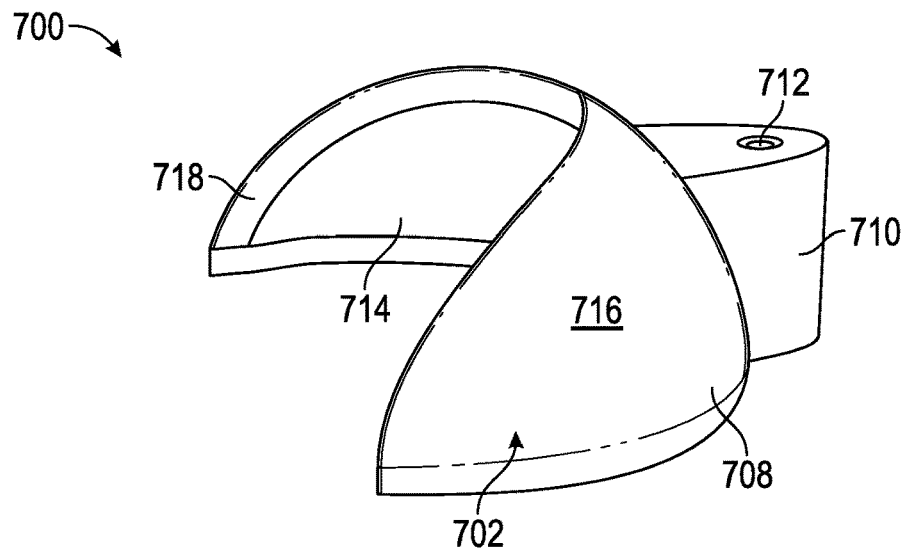
FIG. 19A is a perspective view of another example of a C-shaped glenosphere helper having a moon shape.
Figure 19B:
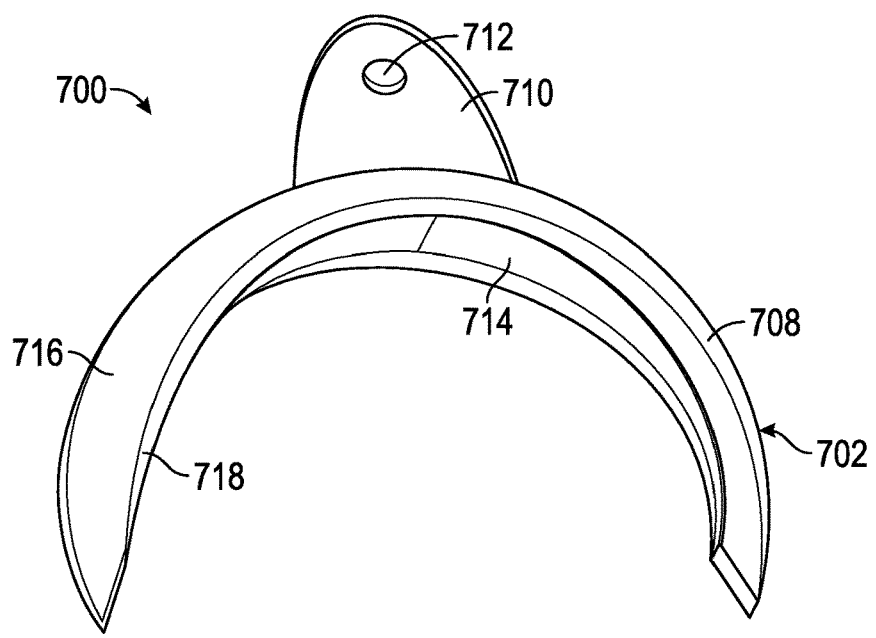
FIG. 19B is another perspective view of the moon-shaped glenosphere helper of FIG. 19A.

FIG. 19A is a perspective view of another example of C-shaped glenosphere helper 700 having a moon shape. FIG. 19B is another perspective view of moon-shaped glenosphere helper 700 of FIG. 19A. Helper 700 includes helper body 702, which includes sidewall 708 and flange 710 having bore 712. Sidewall 708 includes interior surface 714, exterior surface 716 and edge surface 718.

Helper 700 is substantially similar to helper 600 of FIGS. 16A and 16B except that the C-shape of helper body 702 can have the shape of a moon wherein separate end surfaces (e.g. end surfaces 618A and 618B) are blended together to form a single edge surface 718. Edge surface 718 can extend in both the radial and circumferential directions to wrap around center axis $A_1$ of glenosphere 20A (FIG. 16A). Edge surface 718 streamlines the shape of helper 700 in order to facilitate insertion and removal of body 702 from the patient, and also to facilitate easier manufacturing of body 702.

Figure 20A:
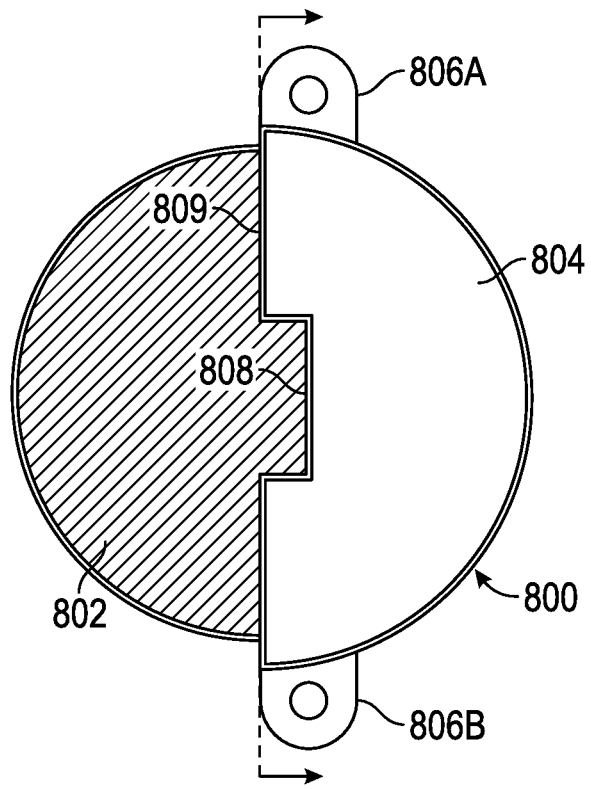
FIG. 20A is a plan view of another example of a glenosphere helper positioned around a glenosphere.

FIG. 20A is a plan view of another example of glenosphere helper 800 positioned around glenosphere 802. Helper 800 includes hemispherical body 804 which includes first flange 806A and second flange 806B, and in which cut-out 808 is disposed. Hemispherical body 804 can have a cup shape that matches the hemispherical shape of glenosphere 802. Body 804 can be a half hemisphere with the addition of cut-out 808. Body 804, thus, can have a D-shape with a semi-circular end wall 809 into which cut-out 808 extends. As such, glenosphere 802 can be retained within body 804 by a self-holding action.

Flanges 806A and 806B can be positioned at ends of body 804. Flanges 806A and 806B permit helper 800 to be attached to superior pin 40 in two orientations. Flange 806A can be used to connect to superior pin 606 when performing arthroplasty on a left shoulder. Flange 806B can be used to connect to superior pin 606 when performing arthroplasty on a right shoulder. In either configuration, end wall 809, and cut-out 808, can face the posterior direction. As such, when flange 806A is connected to superior pin 40 (FIG. 17) on the left side, flange 806B will face the inferior direction. When flange 806B is connected to superior point 40A (FIG. 17) on the right side, flange 806A will face the inferior direction. Such a dual flange configuration eliminates the need for separate parts, and part numbers, for left and right side procedures, as well as avoids posterior interference from a flange.

Cut-out 808 can encompass the center point of glenosphere 802. In other words, cut-out 808 can partially encircle the location of the center axis $A_1$ of glenosphere 802. Cut-out 808 can be shaped to engage with an impactor, such as impactor 812 of FIG. 20B. In particular, cut-out 808 can be shaped to engage with an impactor in only one configuration. As such, cut-out 808 can comprise a fool proofing feature that prevents misalignment between the impactor and glenosphere.

Figure 20B:
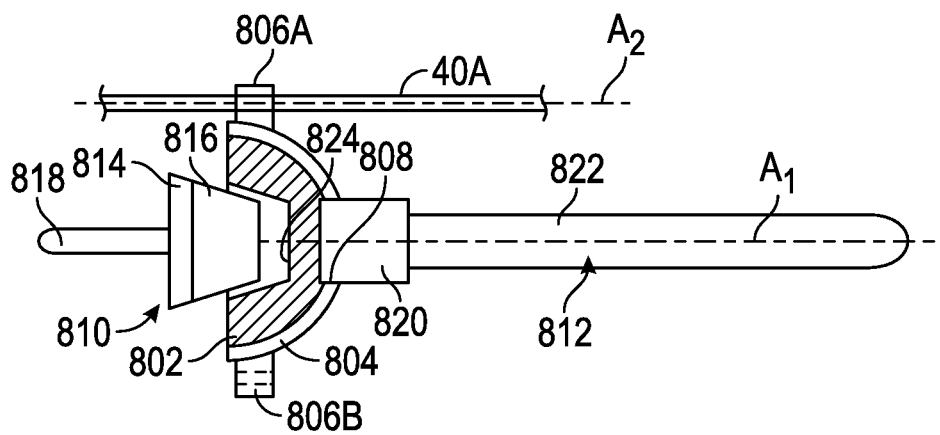
FIG. 20B is a side diagrammatic view of the glenosphere helper of FIG. 20A engaged with a glenosphere baseplate and an impactor.

FIG. 20B is a side diagrammatic view of glenosphere helper 800 of FIG. 20A engaged with glenoid implant 810 and impactor 812. Glenoid implant 810 includes base plate 814, body 816 and peg 818. Impactor 812 includes head 820 and handle 822. Glenosphere 802 includes inner cavity 824.

Glenosphere helper 800 can position the center of glenosphere 802 along axis $A_1$, which can be positioned to co-axially align with peg 818. As discussed, helper 800 can use superior pin 40A to ensure proper alignment that facilitates mounting of glenosphere 802 on implant 810. In particular, it can be desirable for inner cavity 824 to properly align with body 816 to ensure proper seating of the components with each other. In one example, it is desirable that the Morse taper of body 816 properly fit within inner cavity 824 to, among other things, ensure that a humerus liner component properly slides and rotates on glenosphere 802. Hemispherical body 804 includes cut-out 808 that facilitates driving of impactor 812 straight along axis $A_1$ to help ensure that inner cavity 824 is pushed straight down onto body 816. Thus, interaction of flange 806A and superior pin 40A can help ensure that glenosphere 802 makes first contact with implant 810 in proper alignment along axis $A_1$, while cut-out 808 can help ensure that impactor 812 drives glenosphere 802 the last distance down body 816 in proper alignment along axis $A_1$. As mentioned, cut-out 808 encircles the center region of glenosphere 802, including axis $A_1$, to facilitate engagement of impactor 812 and transmission of force from impactor 812 along axis $A_1$. By having the same or a similar shape as head 820, surfaces of body 804 forming cut-out 808 can also engage, or trap, head 820 to prevent impactor 812 from sliding or slipping off of glenosphere 802 during impacting operations. Additionally, the shape of cut-out 808 can help ensure that impactor 812 engages glenosphere 802 in only desirable orientations that can prevent transmission of forces from impactor 812 to glenosphere 802 that are off axis, or angled relative to axis $A_1$. For example, head 820 can be configured to fit into cut-out 808 in only one orientation. In another example, head 820 can be configured to fit into cut-out 808 in two orientations, e.g. including two orientations of impactor 812 rotated one-hundred-eighty degrees from each other.

Figure 21A:
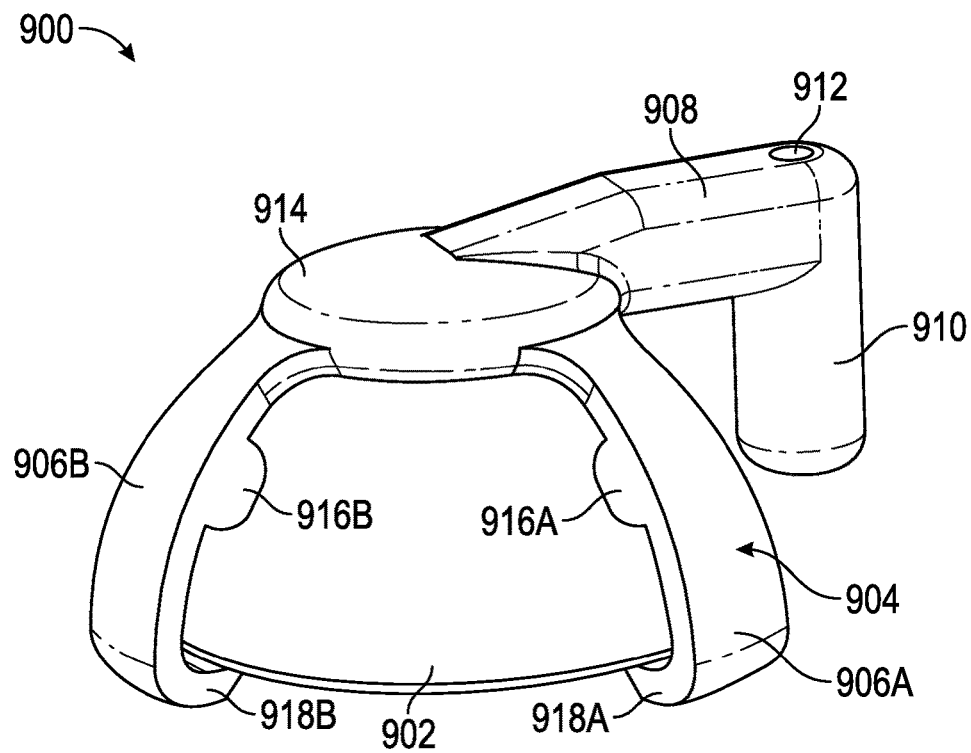
FIG. 21A is a perspective view of another embodiment of a glenosphere helper having a three-prong cup shape.
Figure 21B:
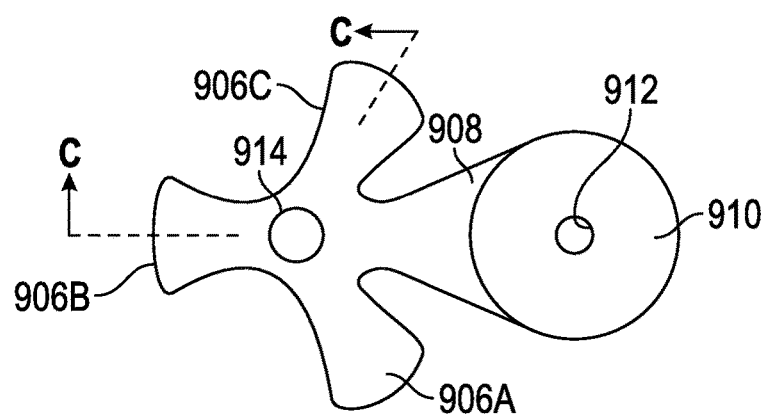
FIG. 21B is a top plan view of the glenosphere helper of FIG. 21A.

FIG. 21A is a perspective view of another embodiment of glenosphere helper 900 having a three-prong cup shape that is positioned around glenosphere 902. FIG. 21B is a top plan view of glenosphere helper 900 of FIG. 21A. Helper 900 includes hemispherical body 904, which includes prongs 906A, 906B and 906C. Flange 908 extends from hemispherical body 904 and is connected to sleeve 901, through which bore 912 extends. Body 904 also includes disk 914, pads 916A and 916B, and tabs 918A and 918B, as well as a pad and tab on prong 906C that are not shown.

Hemispherical body 904 can have a cup shape that matches the hemispherical shape of glenosphere 902, but for the cut-outs formed between prongs 906A-906C. Tabs 918A and 918B (along with tab 918C on prong 906C shown in FIG. 21C) can retain glenosphere 902 in body 904. Pads 916A and 916B (along with a pad not shown on prong 906C) can provide contact points for engaging with glenosphere 902 to reduce contact of body 904 with glenosphere 902 to minimize scratching or blemishing of glenosphere 902. Pads 916A and 916B can also provide fulcrum points for prongs 906A and 906B to bend around glenosphere 902 to allow tabs 918A and 918B to engage the edge of glenosphere 902 while in tension. As such, tabs 918A and 918B may snap around glenosphere 902 to retain glenosphere tightly therein.

As with the examples discussed above, flange 908 can extend beyond the outer periphery or diameter of glenosphere 902 and body 904 to locate a guide pin (e.g. superior pin 40A) that extends through bore 912 away from glenosphere 902 and the implant location. Sleeve 910 can extend from flange 908 perpendicular to the center axis (not shown) of glenosphere 902. Sleeve 910 can add length to bore 912 to provide stability to helper 900 while engaged with a pin (e.g. superior pin 40A) extending through bore 912. In one example, flange 908 and prongs 906A-906C are connected at disk 914.

Disk 914 can be located at the center region of glenosphere 902 and can be shaped to join flange 908 and prongs 906A-906C. Prongs 906A-906C can be spaced equally about disk 914, e.g. one-hundred-twenty degrees apart. Flange 908 can be centered between prongs 906A and 906C.

Disk 914 can also be configured to include a release mechanism for disengaging prongs 906A-906C with glenosphere 902.

Figure 21C:
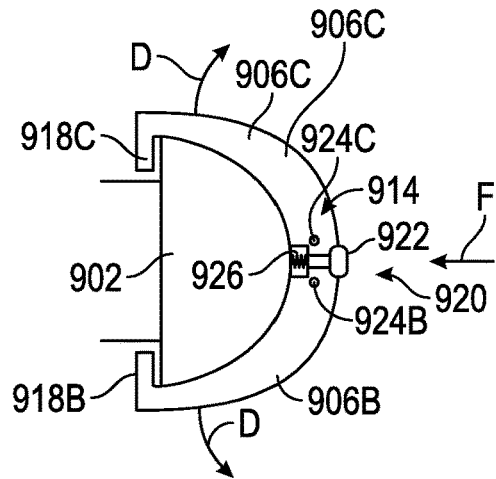
FIG. 21C is a diagrammatic view of the glenosphere helper of FIGS. 21A and 21B showing operation of a release mechanism.

FIG. 21C is a diagrammatic view of glenosphere helper 900 of FIGS. 21A and 21B showing operation of release mechanism 920. Release mechanism 920 may comprise any suitable mechanism such that when force F is applied to disk 914, such as at button 922, prongs 906A-906C are caused to move radially outward in direction D from the center of glenosphere 902 in order to release tabs 918A-918C from glenosphere 902. In one example, prongs 906A-906C can be mounted at disk 914 at pins 924A, 924B and 924C (not shown, but similar in structure to pins 924A and 924B), respectively so as to be rotatable, and button 922 can be advanced inward towards radially inner ends of prongs 906A-906C to rotate radially outer ends of prongs 906A-906C at tabs 918A-918C away from glenosphere 902 in direction D. Additionally, mechanism 920 can include spring 926 or other springs (not shown) to bias button 922 outward and prongs 906A-906C inward toward glenosphere 902. Mechanism 920 can be repeatedly used to engage and disengage glenosphere 902 in a releasable manner. Tabs 918A-918C and pads 916A-916C (not shown in FIG. 21C) can be positioned on prongs 906A-906C to help ensure glenosphere 902 is seated properly within prongs 906A-906C.

Figure 22A:
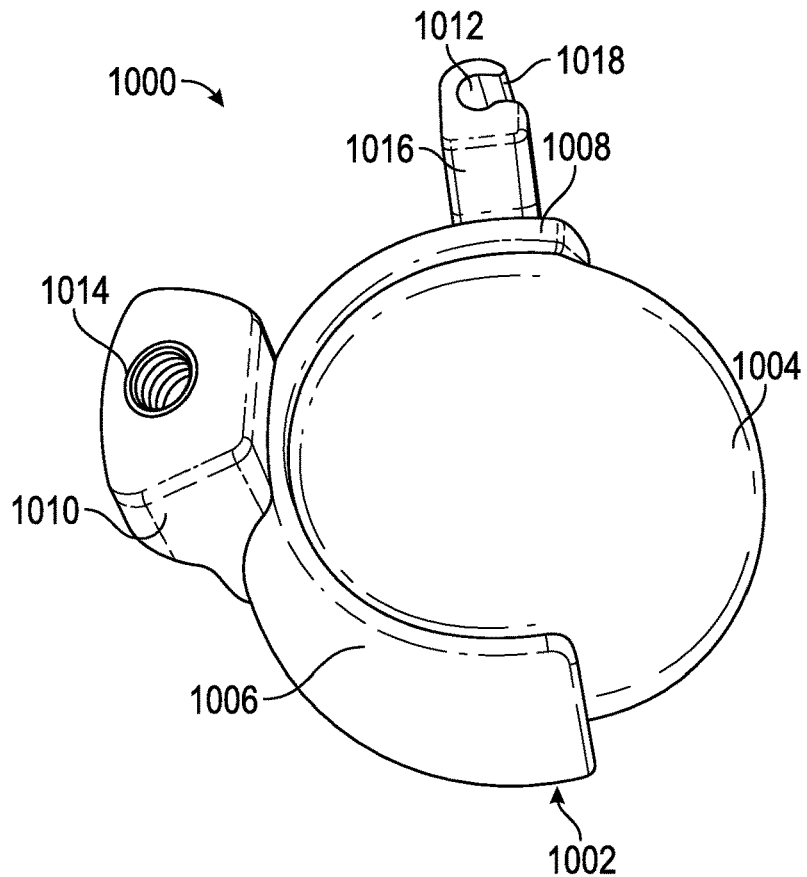
FIG. 22A is a perspective view of another example of a glenosphere helper having an impactor tool socket.
Figure 22B:
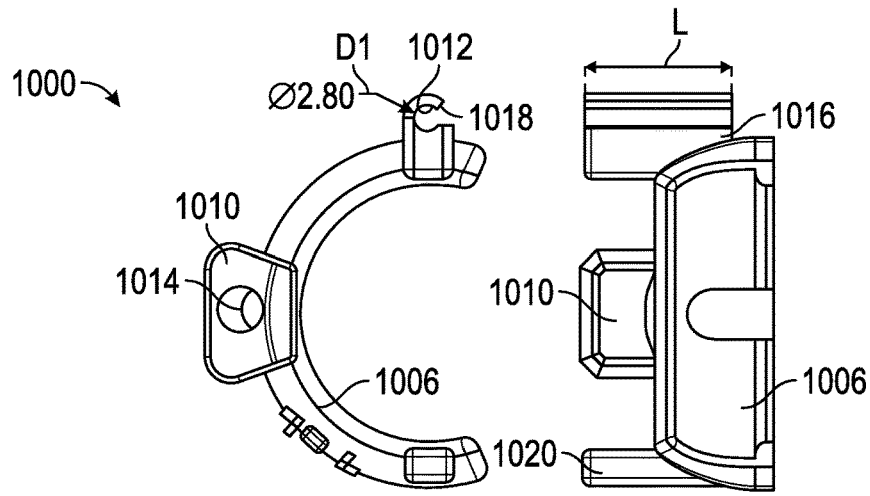
FIGS. 22B-22D are plan and side views of different examples of the glenosphere helper of FIG. 22A.
Figure 22C:
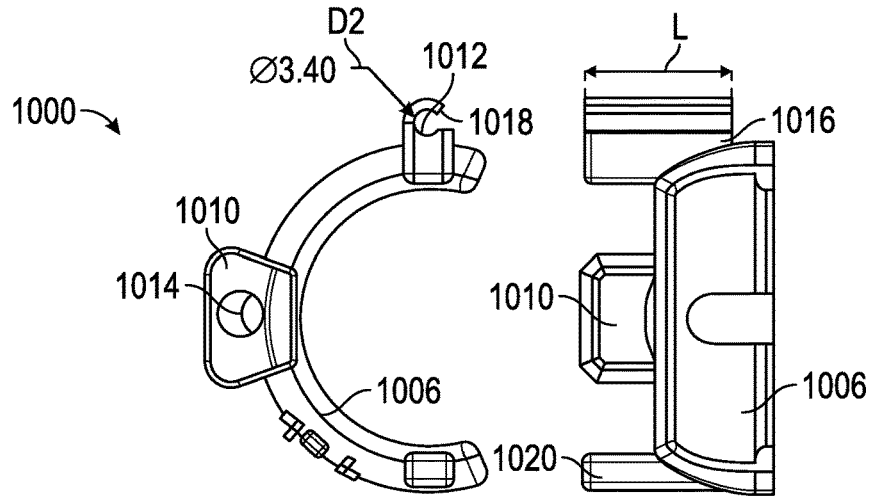
Figure 22D:
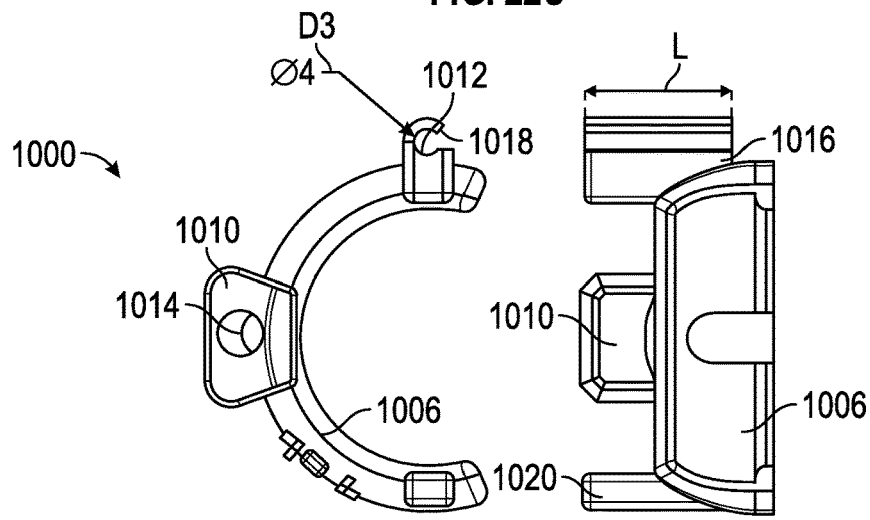

FIG. 22A is a perspective view of another example of glenosphere helper 1000 having an impactor tool socket. Helper 1000 includes C-shaped helper body 1002 coupled to glenosphere 1004. FIGS. 22B-22D are plan and side views of different examples of glenosphere helper 1000 of FIG. 22A. Helper body 1002 includes sidewall 1006, from which flange 1008 and guide 1010 extend. Flange 1008 includes bore 1012, and guide 1010 includes bore 1014. Sidewall 108 can be configured similarly to sidewall 608 (FIGS. 16A and 16B) in one example.

Flange 1008 can be configured similarly to flange 610 (FIGS. 16A and 16B) and also includes sleeve 1016, which can be configured similarly to flange 910 (FIG. 21A), to stabilize a pin (e.g. superior pin 40A) inserted within bore 1012. As indicated in FIGS. 22B-22D, sleeve 1016 can have a length L of approximately 17 mm to inhibit helper 1000 from rocking or tilting on a pin in one example. In other examples, sleeve 1016 can have other lengths. Flange 1008, including sleeve 1016, can be notched to include a cut-out 1018 that allows flange 1008 to be slipped over and clipped on a pin such that helper 1000 need not have to be positioned at a lateral end of the pin to couple to the pin. Notch 1018 can be big enough to allow flange 1008 to flex and slip over the pin, but small enough to allow helper 1000 to be tightly engaged with the pin to limit rotation such as due to friction. As shown in FIGS. 22B-22D, bore 1012 can be sized to engage with different diameter pins, such as diameter D1 in FIG. 22B, diameter D2 in FIG. 22C and diameter D3 in FIG. 22D. For example, bore 1012 can be approximately 4 mm, approximately 3.4 mm or approximately 2.8 mm in diameter.

Guide 1010 can be positioned in close proximity to sidewall 1008 and bore 1014 can be threaded to receive a threaded shaft of an impactor, such as a dual taper/spacer impactor as is known in the art. In one example, bore 1014 can include a metal insert that provides threading for engaging mating threading of an impactor. Bore 1014 can be positioned such that the center axis of bore 1014 angles towards glenosphere 1004. In other examples, bore 1014 is tangent to or extends to the interior of glenosphere 1004.

Furthermore, as shown in FIGS. 22B-22D, helper 1000 includes tab 1020 projecting from sidewall 106 to facilitate grasping of helper 1000. Tab 1020 is illustrated as having a rectilinear cross-section with rounded edges and corners. However, in other examples, any shaped projection can be used. Tab 1020 and other configurations of projections for facilitating grasping of the glenosphere helper can be combined with any of the examples and embodiments of glenosphere helpers described herein above. Tab 1020 allows a physician, or anyone who is implanting glenosphere 1004, to easily manipulate glenosphere 1004 while seated in helper 1000. In particular, tab 1020 allows a physician to feel engagement between the Morse taper of the body of an implant and the socket of a glenosphere.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A glenosphere helper comprising:
   a C-shaped body having an interior surface curved around a central axis for engaging at least a portion of an outer surface of a glenosphere, the interior surface of the C-shaped body having a shape configured to mate with a hemi-spherical shaped glenosphere;
   a flange extending from the c-shaped body to receive a guide pin at a point on the flange, wherein the point comprises a bore extending through the flange such that the guide pin is configured to extend along a slide axis parallel to the central axis, the flange extending from the c-shaped body such that the point is positioned outside a periphery of the glenosphere; and
   a guide having a threaded bore, the guide positioned such that the threaded bore is configured to be angled toward the glenosphere.

2. The glenosphere helper of claim 1, wherein the C-shaped body is open at a center of the C-shaped body.

3. The glenosphere helper of claim 2, wherein the C-shaped body has a pair of circumferential ends that are configured to be approximately one-hundred-eighty degrees apart around a circumference of the glenosphere.

4. The glenosphere helper of claim 2, wherein the flange extends from an end of the C-shape.

5. The glenosphere helper of claim 1, further comprising a sleeve surrounding the bore.

6. The glenosphere helper of claim 1, further comprising the guide pin, the guide pin having an outer diameter that is smaller than an inner diameter of the bore.

7. The glenosphere helper of claim 1, wherein the c-shaped body includes tabs that project therefrom that.

8. The glenosphere helper of claim 1, wherein the c-shaped body comprises a polymeric material.

9. A system for implanting a glenosphere, the system comprising:
   a glenosphere having a hemispherical outer surface, an inner cavity disposed opposite the hemispherical outer surface and being configured to receive a body extending from a baseplate of an implant and a center location located at a center of the hemispherical outer surface through which a center axis of the glenosphere extends perpendicular to the hemispherical outer surface;
   a glenosphere helper having a body comprising:
      an interior surface for engaging the outer surface around the center location;
      a flange extending away from the body transverse to the center axis beyond an outer circumferential periphery of the glenosphere; and
      a guide having a threaded bore, the guide positioned such that the threaded bore is configured to be angled toward the glenosphere; and
   a guide pin extending through the flange parallel to the center axis;
   wherein the glenosphere helper is configured to receive the glenosphere and the glenosphere helper is configured to slide along the guide pin to guide the glenosphere onto the body of the baseplate.

10. The system of claim 9, wherein:
    the flange includes a bore configured to form a force fit with the guide pin; and the body of the glenosphere helper is C-shaped to wrap partially around the center axis.

11. The system of claim 9, further comprising the baseplate and the body extending from the baseplate, wherein the glenosphere and the baseplate are non-articulating.

12. The system of claim 11, wherein the baseplate includes a peg or fixation screws for securing the baseplate to a scapula.

13. The system of claim 12, wherein the body extending from the base plate includes a tapered outer surface configured to mate with the inner cavity of the glenosphere, wherein the glenosphere is configured to mate with the glenosphere helper such that when the glenosphere helper is slid along the guide pin, the interior cavity of the glenosphere will seat on the tapered outer surface of the body of the base plate.

14. The system of claim 9, wherein the interior surface of the glenosphere helper has a shape to match the hemispherical outer surface of the glenosphere.

15. A method for implanting a glenosphere, the method comprising:
    installing a first pin in a glenoid cavity;
    installing an implant in the glenoid cavity; and
    guiding a glenosphere onto the implant using a helper connected to the first pin,
    the glenosphere comprising:
        a hemispherical outer surface, an inner cavity disposed opposite the hemispherical outer surface and being configured to receive a body extending from a baseplate of the implant and a center location located at a center of the hemispherical outer surface through which a center axis of the glenosphere extends perpendicular to the hemispherical outer surface;
    the helper comprising:
        a C-shaped body having an interior surface curved around the central axis for engaging at least a portion of the hemispherical outer surface of the glenosphere, the interior surface of the C-shaped body having a shape configured to mate with the hemispherical outer surface of the glenosphere;
        a flange extending from the c-shaped body to receive the first pin at a point on the flange, wherein point comprises a bore extending through the flange such that the first pin is configured to extend along a slide axis parallel to the central axis, the flange extending from the body such that the point is positioned outside a periphery of the glenosphere; and the helper further comprising
        a guide having a threaded bore, the guide positioned such that the threaded bore is configured to be angled toward the glenosphere.

16. The method of claim 15, further comprising:
    rotating the helper on the first pin to position the glenosphere toward the body of the baseplate of the implant; and
    seating the glenosphere onto the mounting surface of the implant.

17. The method of claim 15, wherein:
    the helper is a patient specific component configured such that a distance between the center location and the bore is specific to a patient.

18. The method of claim 15, wherein installing the first pin comprises:
    connecting a glenosphere trial to the implant;
    connecting the helper to the glenosphere trial; and
    installing the first pin at a location determined by the helper.

19. The method of claim 15, wherein installing the first pin comprises:
    installing a second pin; and
    using a patient specific instrument that sets a distance between the first pin and a second guide pin; and installing the second guide pin.

\* \* \* \* \*

UNITED STATES PATENT AND TRADEMARK OFFICE
CERTIFICATE OF CORRECTION

PATENT NO. : 10,426,624 B2
APPLICATION NO. : 15/155840
DATED : October 1, 2019
INVENTOR(S) : Van Kampen et al.

Page 1 of 1

It is certified that error appears in the above-identified patent and that said Letters Patent is hereby corrected as shown below:

In the Claims

In Column 20, Line 33, in Claim 19, after "comprises:", delete "installing a second pin; and"

Signed and Sealed this
Second Day of June, 2020

Andrei Iancu
*Director of the United States Patent and Trademark Office*